(12) United States Patent
Basu et al.

(10) Patent No.: US 9,023,837 B2
(45) Date of Patent: May 5, 2015

(54) ANDROGEN INDUCED OXIDATIVE STRESS INHIBITORS

(75) Inventors: Hirak S. Basu, Madison, WI (US); David A. Zarling, Menlo Park, CA (US); George Wilding, Verona, WI (US); Farideh Mehraein-Ghomi, Madison, WI (US); Dawn R. Church, Stoughton, WI (US)

(73) Assignee: Colby Pharmaceutical Company, Menlo Park, CA (US)

( * ) Notice: Subject to any disclaimer, the term of this patent is extended or adjusted under 35 U.S.C. 154(b) by 0 days.

(21) Appl. No.: 13/641,662

(22) PCT Filed: Apr. 15, 2011

(86) PCT No.: PCT/US2011/032766
§ 371 (c)(1),
(2), (4) Date: Apr. 26, 2013

(87) PCT Pub. No.: WO2011/130692
PCT Pub. Date: Oct. 20, 2011

(65) Prior Publication Data
US 2013/0210772 A1    Aug. 15, 2013

Related U.S. Application Data

(60) Provisional application No. 61/471,047, filed on Apr. 1, 2011, provisional application No. 61/325,251, filed on Apr. 16, 2010.

(51) Int. Cl.
*C07D 311/42*  (2006.01)
*C07D 405/12*  (2006.01)
*C07D 311/56*  (2006.01)
*C07D 487/04*  (2006.01)

(52) U.S. Cl.
CPC .......... *C07D 311/42* (2013.01); *C07D 311/56* (2013.01); *C07D 487/04* (2013.01); *C07D 405/12* (2013.01)

(58) Field of Classification Search
None
See application file for complete search history.

(56) References Cited

U.S. PATENT DOCUMENTS

| | | |
|---|---|---|
| 2003/0096860 A1 | 5/2003 | Takagaki et al. |
| 2008/0020068 A1 | 1/2008 | Germer et al. |
| 2008/0319054 A1 | 12/2008 | Kun et al. |

FOREIGN PATENT DOCUMENTS

| | | | |
|---|---|---|---|
| JP | 09-020778 A | | 1/1997 |
| WO | WO03050105 | * | 6/2003 |
| WO | WO 2011/130692 A2 | | 10/2011 |

OTHER PUBLICATIONS

Mehraein-Ghomi et al. JunD Mediates Androgen-Induced Oxidative Stress in Androgen Dependent LNCaP Human Prostate Cancer Cells. The Prostate, 2008, 68, 924-934.*
Ito et al., A medium-term rat liver bioassay for rapid in vivo detection of carcinogenic potential of chemicals. Cancer Science 2003, 94, 3-8.*
CAPLUS printout of Bravo et al., Oxygen heterocycles by sulfur ylide annulation. IX. 3,4-Dihydro-2-(hydroxymethyl)-2H,5H-pyrano[3,2c][1]benzopyran-5-ones from 3-(3-oxoalkyl)-4-hydroxycoumarins and dimethylsulfoxonium methylide. Gazzetta Chimica Italiana, 1986, 116, 501-510.*
CAPLUS printout of Covello et al., New iodoorganic compounds. Iodo derivatives of 4-hydroxycoumarin. Annali di Chimica, 1968, 58, 895-902.*
Katayama, et al. Anti-cancer activities of pyrazolo[1,5-a]indole derivatives. Chem Pharm Bull (Tokyo). Nov. 2000;48(11):1628-1633.
Katayama, et al. Synthetic dual inhibitors of DNA topoisomerase I and II. Chem Pharm Bull (Tokyo). Jan. 1996;44(6):1276-1278.
Katayama, et al. Synthetic inhibitors of DNA topoisomerase I and II. Chem Pharm Bull (Tokyo). Jan. 1999;47(1):48-53.
PCT/US2011/032766 International Search Report & Written Opinion dated Dec. 7, 2011.
PCT/US2011/032766 International Preliminary Report on Patentability dated Oct. 16, 2012.
Umemura, et al. Inhibition of DNA topoisomerases II and/or I by pyrazolo[1,5-a]indole derivatives and their growth inhibitory activities. Mol Pharmacol. Oct. 2002;62(4):873-880.

* cited by examiner

*Primary Examiner* — Michael Barker
*Assistant Examiner* — Po-Chih Chen
(74) *Attorney, Agent, or Firm* — Wilson Sonsini Goodrich & Rosati

(57) ABSTRACT

Described herein are pharmaceutical compositions and medicaments, and methods of using such pharmaceutical compositions and medicaments in the treatment of cancer.

13 Claims, 21 Drawing Sheets

FIG. 2
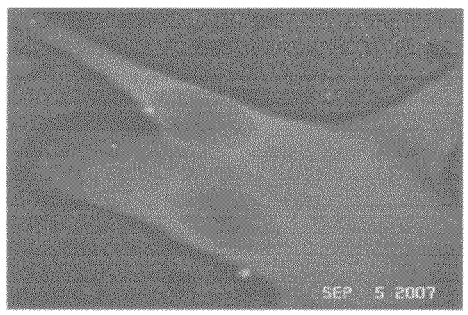

FIG. 5

A     ChIP

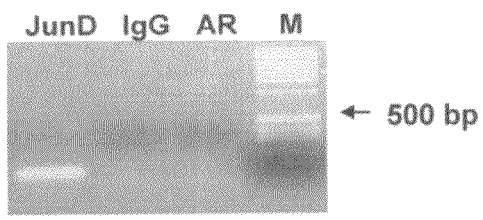

B     Sequence of *SSAT* promoter recovered by ChIP assay

-574

541 GGTGGCAGGT GGGAGGCTGA AGCAGGAGAA TCACTTGAAC CCAGGAGGAG GCGGAGGTTG
601 CAGTGAGCCG AGATTGTGCC ATTGCACTCC AGCCTGGGCA ATAGAGTGAG ACTCTGTTTA
661 AAAAAAAAAT ATATATATAT ATATATATAA TATATATATA TTATATATAT ATATATAATA
721 TATATATATA TTATATATAT ATATGTAATG TTGGTTGCAT CTATCCATTC ATGACAATGG
781 AAAAGCATAA TGTGATTCAC TGCCATGAAA AACATTCAAA CTTCTTAGGG TTCTAGGCTT

FIG. 7A. Androgen induced SSAT induction in prostate cells causes spermidine/spermine oxidation and ROS production.

FIG. 8. Luciferase reporter activity in SSAT-luc transfected control and JunD silenced (siJunD) LNCaP cells either vehicle treated (black bar) or treated with 1nM R1881 (grey bar).

FIG. 9. (A) Vector inserts with GL-AR and JunD-GL. (B) GL activity without (black bar) or with (grey bar) R1881 treatment.

FIG. 10. (A) Effect of 2,2'-(hydrazine-1,1-diyl)diacetic acid on ROS level of control (circle) and R1881 (square) treated LNCaP cells. (B) Effect of 2,2'-(hydrazine-1,1-diyl)diacetic acid on the growth of control (circle) and R1881 (inverted triangle) treated LNCaP cells.

FIG. 12. Effect of (A) 2,2'-(hydrazine-1,1-diyl)diacetic acid, (B) dimethyl 2,2'-(hydrazine-1,1-diyl)diacetate and (C) 2,2'-(1,3-dioxoisoindolin-2-ylazanediyl)diacetic acid on the ROS levels of LNCaP cells in the absence (circle___) or presence ( inverted triangle___) of 1 nM R1881

FIG. 13A Bicalutamide
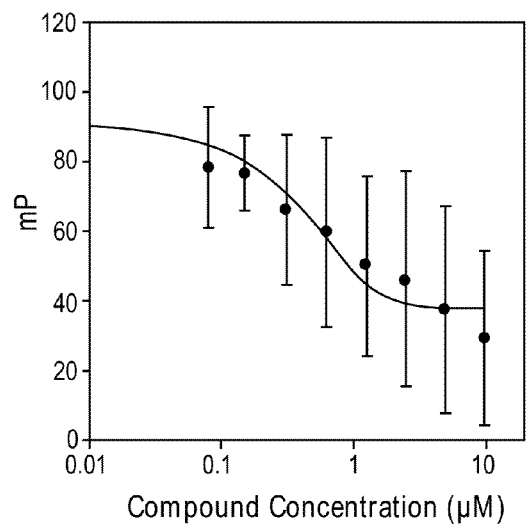
FIG. 13B Compound 81
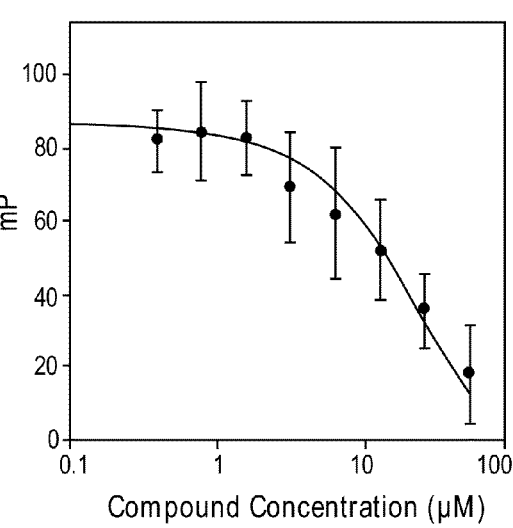
FIG. 13C Compound 71
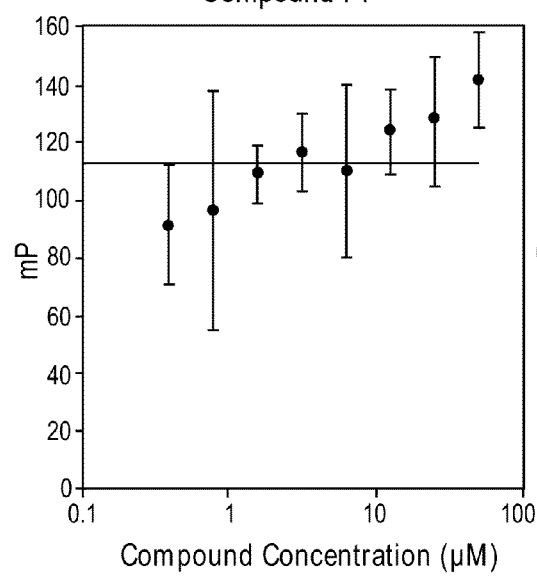
FIG. 13D Compound 31
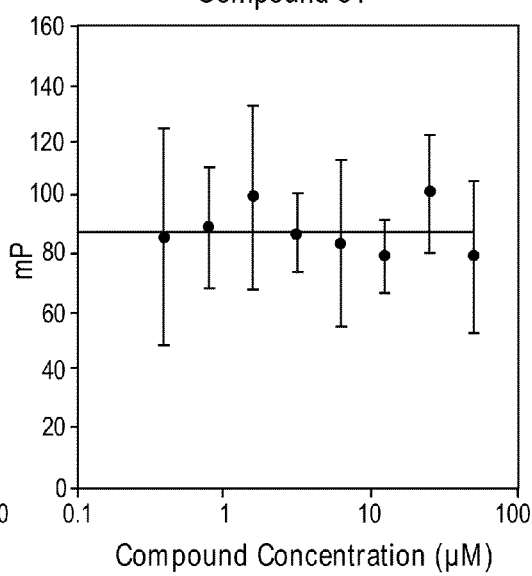

FIG.14A
| Compound | Structure | Classification |
|---|---|---|
| 11 | 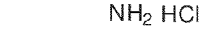 | Non-antiandrogen |
| 12 | 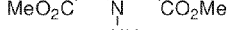 | antiandrogen |
| 13 | 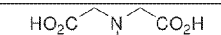 | Non-antiandrogen |
| 21 | 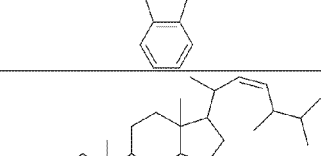 | Non-antiandrogen |
| 31 | 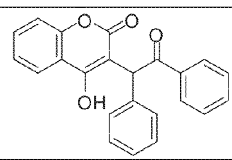 | Non-antiandrogen |
| 41 | 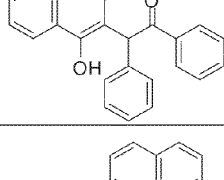 | antiandrogen |
| 51 | 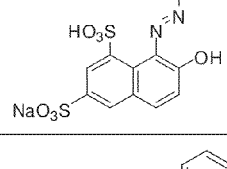 | antiandrogen |
| 61 | 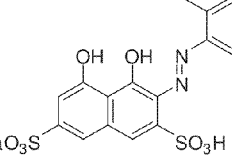 | antiandrogen |

FIG. 14B

| | | |
|---|---|---|
| 71 | *structure: indole-pyrazolium with NMe2, HO, CF3SO3⁻, Me, phenyl substituents* | Non-antiandrogen |
| 81 | *structure: anthraquinone azo compound with CO2H, OH, SO3H* | antiandrogen |
| 91 | *structure: naphthalene bis-sulfonate azo compound with OH, OH, NH2, NaO3S, SO3Na* | Non-antiandrogen |
| bicalutamide | *structure: bicalutamide with CF3, NC, F, OH, sulfone* | Clinical antiandrogen | n.e. = not evaluable due to extremely low DNA

FIG. 18
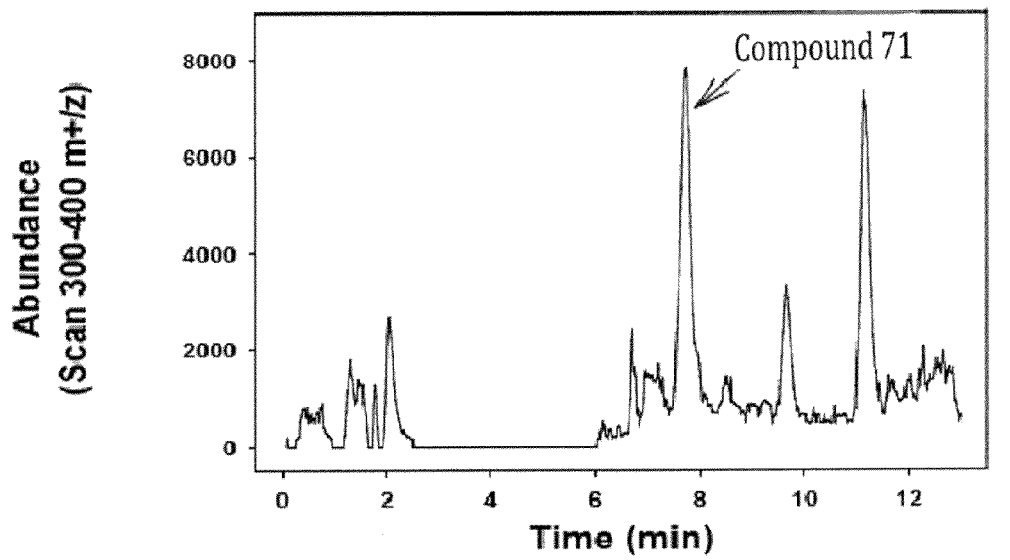
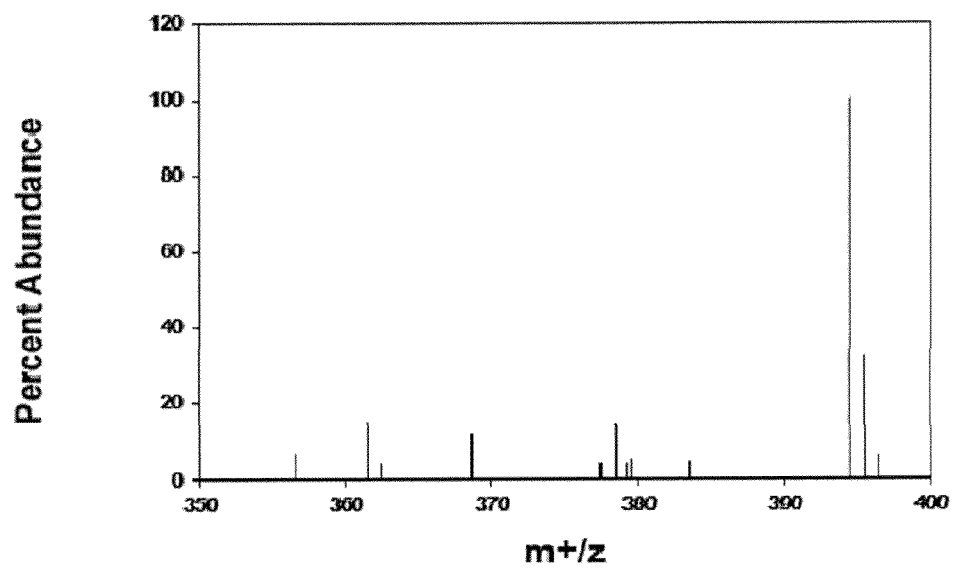

FIG. 19. Effect of 71 on ROS (open circle) and Growth (filled circle) treated androgen-independent LNCaP C4-2 cells growing in low androgen (F1/C4) media.

ANDROGEN INDUCED OXIDATIVE STRESS INHIBITORS

CROSS REFERENCE

This application is a 371 application, filed Apr. 26, 2013, which is a National Stage Application of PCT/US2011/32766, filed Apr. 15, 2011; which claims the benefit of U.S. Provisional Application No. 61/471,047, filed Apr. 1, 2011; and U.S. Provisional Application No. 61/325,251, filed Apr. 16, 2010, all of which are entitled, "ANDROGEN INDUCED OXIDATIVE STRESS INHIBITORS" and herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Feb. 28, 2014, is named 38202-705-831SE-Q.txt and is 980 bytes in size.

FIELD OF THE INVENTION

The present disclosure relates to pharmaceutical compositions which disrupt the JunD-AR interaction and methods for using the same. Described herein are molecules that interact with the binding site(s) and disrupt the JunD-AR interaction. Further, the inhibitors of the AR-JunD interaction, in some embodiments inhibit androgen-induced reactive oxygen species (ROS) production in androgen dependent prostate cancer cells, and prevent prostate cancer occurrence, recurrence and progression.

BACKGROUND OF THE INVENTION

Advanced hormone refractory metastatic prostate cancer (PCa) is the second leading cause of cancer deaths of US men. PCa recurs in approximately 30% of men after their initial treatments of either radical prostatectomy or ionizing radiation therapy. Although Androgen-Deprivation Therapy (ADT) initially causes a regression of the early-stage recurrent PCa, over 80% of the patients under ADT will eventually progress to androgen-independent castration-resistant prostate cancer (CRPCa). Due to the lack of long term benefit of ADT and high frequency of adverse side effects associated with ADT, the identification of a novel agent to prevent PCa progression at an early stage of recurrence is of significant clinical interest.

Cellular Reactive Oxygen Species (ROS) are naturally occurring agents that cause DNA, RNA, lipid and protein damage if their concentrations become too high. ROS levels have been established to be distinctly higher in PCa tissue than in normal prostate. ROS have been shown to propagate prostate cancer development, not only by causing DNA damage, but also by activating an androgen independent survival pathway. Published data have confirmed that androgens induce ROS production in PCa cells via two major factors. First, transcription factor JunD is overexpressed in human PCa cells, when androgen induces oxidative stress, and secondly androgen induces up-regulation of spermidine/spermine acetyl transferase (SSAT), an enzyme responsible for spermidine and spermine catabolism that leads to a rise in cellular ROS levels. In addition, recent data further suggest an intriguing mechanism of PCa progression, where AR-JunD induced SSAT expression causing an increase in ROS levels and consequent upregulation of the transcription factor NF-κB may set up an autocrine feed forward loop of SSAT-ROS-NFκB-SSAT that can sustain ROS production and PCa cell proliferation in the absence of androgen.

Disclosed herein are inhibitors of AR-JunD interaction, which disrupt the AR-JunD complex in PCa cells and thus, block the ROS production, NF-κB activation, and prevent PCa progression. In some embodiments, these inhibitors are effective therapeutic agents for treatment of both androgen-dependent and castrate-resistant prostate cancer.

Androgen activation of AR in LNCaP human PCa cells induces AP-1 transcription factors Fra-2 and JunD. However, only JunD levels and its functional activity remained elevated for 96 h after androgen treatment, when androgen-induced ROS production is observed. JunD may either inhibit or help cellular ROS production, depending on cell type, presence of ROS-generating proteins, growth conditions, etc. Since androgen-induced ROS generation is abrogated by either blocking androgen-induced JunD over-expression with the anti-androgen bicalutamide or silencing JunD protein expression using siRNA, thus JunD activity is deemed necessary for androgen-induced oxidative stress in LNCaP cells.

SUMMARY OF THE INVENTION

Presented herein are compounds, including pharmaceutical compositions, which bind to and disrupt the JunD-AR interactions by binding to specific sites. Described herein are also agents that disrupt the interaction between the androgen receptor and the transcription factor, JunD, to prevent progression of hormone-refractory prostate cancer by inhibition of oxidative stress generating pathways.

In one aspect is a compound having the structure of Formula (I):

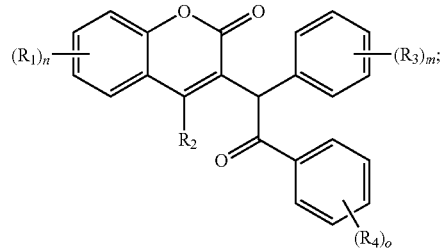

Formula (I)

wherein:

$R_1$, $R_3$ and $R_4$ are each independently selected from H, D, F, Cl, Br, I, —CN, —$NO_2$, —OH, —$CF_3$, —$OCF_3$, —$OR_4$, —$NR_6R_6$, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, optionally substituted aryl, optionally substituted O-aryl, optionally substituted heteroaryl, —N=N-aryl, —NHS(=O)$_2R_5$, —S(=O)$_2$N($R_6$)$_2$, —N($R_6$)S(=O)$_2$N($R_6$)$_2$, —C(=O)$CF_3$, —C(=O)NHS(=O)$_2R_5$, —S(=O)$_2$NHC(=O)$R_5$, —N($R_6$)$_2$, —N($R_6$)C(=O)$R_6$, —N($R_6$)C(=O)N($R_6$)$_2$, —N($R_6$)C(=O)O$R_5$, —$CO_2R_6$, —C(=O)$R_6$, —OC(=O)$R_5$, —OC(=O)N($R_6$)$_2$, —CON($R_6$)$_2$, —$SR_6$, —S(=O)$R_5$, and —S(=O)$_2R_5$;

each $R_5$ is independently selected from $C_1$-$C_6$alkyl, $C_1$-$C_6$haloalkyl, $C_3$-$C_8$cycloalkyl, aryl, and benzyl;

each $R_6$ is independently selected from H, $C_1$-$C_6$alkyl, $C_1$-$C_6$haloalkyl, $C_3$-$C_8$cycloalkyl, aryl, and benzyl;

$R_2$ is selected from H, OH, OC(=O)$C_1$-$C_6$alkyl, or OC(=O)H;

n is an integer selected from 0-4;

m and o are each independently an integer selected from 0-5;

or a pharmaceutically acceptable salt, solvate, prodrug or metabolite thereof.

In one embodiment is the compound of Formula (I) wherein $R_2$ is OH. In another embodiment is the compound of Formula (I) wherein $R_2$ is $OC(=O)C_1$-$C_6$alkyl. In yet another embodiment is the compound of Formula (I) wherein $C_1$-$C_6$alkyl is selected from methyl, ethyl, n-propyl, iso-propyl, n-butyl, iso-butyl, or tert-butyl. In a further embodiment is the compound of Formula (I) wherein $R_1$ is $S(=O)_2OH$. In yet a further embodiment is the compound of Formula (I) wherein $R_1$ is —N=N-aryl. In one embodiment is the compound of Formula (I) wherein aryl is naphthyl. In another embodiment is the compound of Formula (I) wherein aryl is phenyl. In yet another embodiment is the compound of Formula (I) wherein $R_1$ is OH. In a further embodiment is the compound of Formula (I) wherein n is 1. In one embodiment is the compound of Formula (I) wherein n is 2. In one embodiment is the compound of Formula (I) wherein $R_3$ is $S(=O)_2OH$. In another embodiment is the compound of Formula (I) wherein $R_3$ is —N=N-aryl. In yet another embodiment is the compound of Formula (I) wherein aryl is naphthyl. In a further embodiment is the compound of Formula (I) wherein aryl is phenyl.

In yet a further embodiment is the compound of Formula (I) wherein $R_3$ is —$S(=O)_2N(R_6)_2$. In one embodiment is the compound of Formula (I) wherein $R_6$ is H. In another embodiment is the compound of Formula (I) wherein $R_6$ is heteroaryl. In yet another embodiment is the compound of Formula (I) wherein heteroaryl is pyridine. In a further embodiment is the compound of Formula (I) wherein m is 0. In yet a further embodiment is the compound of Formula (I) wherein m is 1. In one embodiment is the compound of Formula (I) wherein m is 2. In another embodiment is the compound of Formula (I) wherein $R_4$ is $S(=O)_2OH$. In yet another embodiment is the compound of Formula (I) wherein $R_4$ is —N=N-aryl. In a further embodiment is the compound of Formula (I) wherein aryl is naphthyl. In yet a further embodiment is the compound of Formula (I) wherein aryl is phenyl. In one embodiment is the compound of Formula (I) wherein $R_4$ is —$S(=O)_2N(R_6)_2$. In another embodiment is the compound of Formula (I) wherein $R_6$ is H. In yet another embodiment is the compound of Formula (I) wherein $R_6$ is heteroaryl. In a further embodiment is the compound of Formula (I) wherein heteroaryl is pyridine. In yet a further embodiment is the compound of Formula (I) wherein o is 0. In one embodiment is the compound of Formula (I) wherein o is 1. In another embodiment is the compound of Formula (I) wherein o is 2.

In one aspect is a compound selected from the group consisting of:

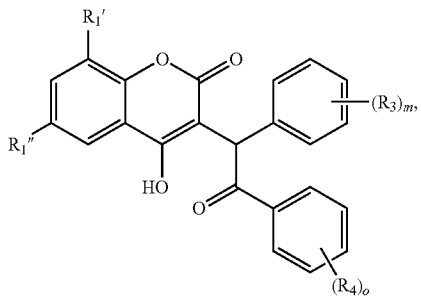

Formula (IA)

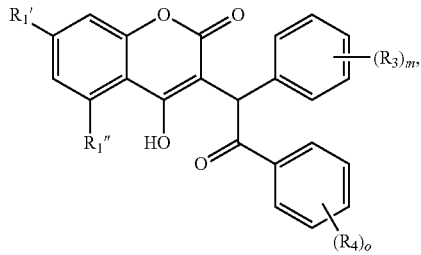

Formula (IB)

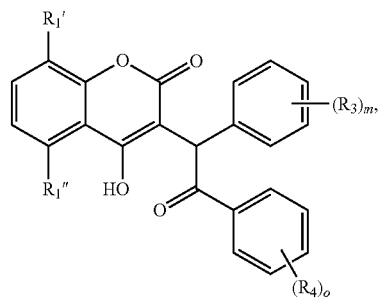

Formula (IC)

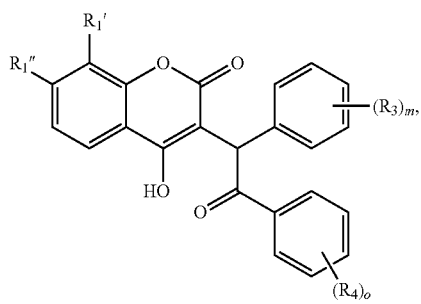

Formula (ID)

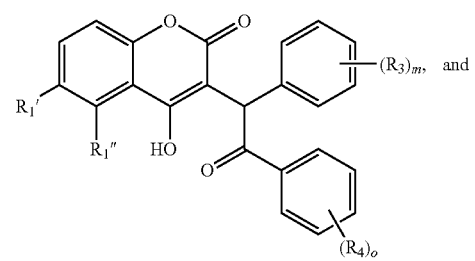

Formula (IE)

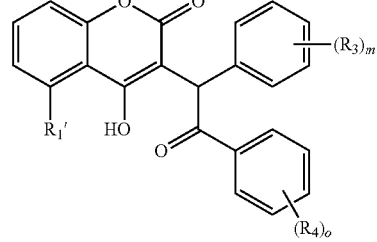

Formula (ID)

wherein $R_1'$ and $R_1''$ are each independently selected from D, F, Cl, Br, I, —CN, —$NO_2$, —OH, —$CF_3$, —$OCF_3$, —$OR_4$, —$NR_6R_6$, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, optionally substituted aryl, optionally substituted O-aryl, optionally substituted heteroaryl, —N=N-aryl, —NHS$(=O)_2R_5$, —$S(=O)_2N(R_6)_2$, —$N(R_6)S(=O)_2N(R_6)_2$, —C(=O)CF₃, —C(=O)NHS(=O)₂R₅, —S(=O)₂NHC(=O)R₅, —N(R₆)₂, —N(R₆)C(=O)R₆, —N(R₆)C(=O)N(R₆)₂, —N(R₆)C(=O)OR₅, —CO₂R₆, —C(=O)R₆, —OC(=O)R₅, —OC(=O)N(R₆)₂, —CON(R₆)₂, —SR₆, —S(=O)R₅, and —S(=O)₂R₅;

each R₅ is independently selected from C₁-C₆alkyl, C₁-C₆haloalkyl, C₃-C₈cycloalkyl, aryl, and benzyl; and each R₆ is independently selected from H, C₁-C₆alkyl, C₁-C₆haloalkyl, C₃-C₈cycloalkyl, aryl, and benzyl.

In another aspect is a compound having the structure of Formula (II) or (III):

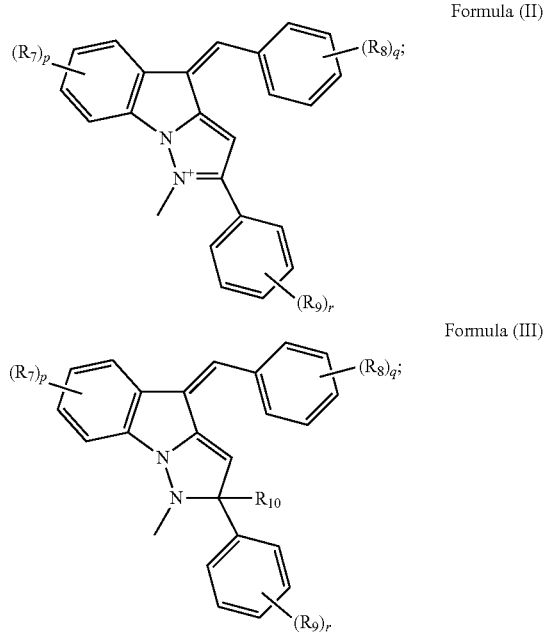

wherein:

R₇, R₈ and R₉ are each independently selected from H, D, F, Cl, Br, I, —CN, —NO₂, —OH, —CF₃, —OCF₃, —OR₄, —NR₆R₆, C₁-C₆alkyl, C₃-C₈cycloalkyl, C₁-C₆heteroalkyl, C₁-C₆haloalkyl, C₂-C₈heterocycloalkyl, optionally substituted aryl, optionally substituted O-aryl, optionally substituted heteroaryl, —N=N-aryl, —NHS(=O)₂R₅, —S(=O)₂N(R₆)₂, —N(R₆)S(=O)₂N(R₆)₂, —C(=O)CF₃, —C(=O)NHS(=O)₂R₅, —S(=O)₂NHC(=O)R₅, —N(R₆)₂, —N(R₆)C(=O)R₆, —N(R₆)C(=O)N(R₆)₂, —N(R₆)C(=O)OR₅, —CO₂R₆, —C(=O)R₆, —OC(=O)R₅, —OC(=O)N(R₆)₂, —CON(R₆)₂, —SR₆, —S(=O)R₅, and —S(=O)₂R₅;

each R₅ is independently selected from C₁-C₆alkyl, C₁-C₆haloalkyl, C₃-C₈cycloalkyl, aryl, and benzyl;

each R₆ is independently selected from H, C₁-C₆alkyl, C₁-C₆haloalkyl, C₃-C₈cycloalkyl, aryl, and benzyl;

R₁₀ is H or C₁-C₆alkyl;

p is an integer selected from 0-4;

q and r are each independently an integer selected from 0-5; or a pharmaceutically acceptable salt, solvate, prodrug or metabolite thereof.

In one embodiment is the compound of Formula (I) wherein R₇ is OH. In another embodiment is the compound of Formula (I) wherein p is 1. In yet another embodiment is the compound of Formula (I) wherein p is 2. In a further embodiment is the compound of Formula (I) wherein R₈ is NR₆R₆. In yet a further embodiment is the compound of Formula (I) wherein each R₆ is H. In one embodiment is the compound of Formula (I) wherein each R₆ is C₁-C₆alkyl. In another embodiment is the compound of Formula (I) wherein C₁-C₆alkyl is selected from methyl, ethyl, n-propyl, iso-propyl, n-butyl, iso-butyl, or tert-butyl. In yet another embodiment is the compound of Formula (I) wherein C₁-C₆alkyl is selected from methyl. In a further embodiment is the compound of Formula (I) wherein q is 1. In yet a further embodiment is the compound of Formula (I) wherein q is 2. In one embodiment is the compound of Formula (I) wherein R₈ is —N=N-aryl. In one embodiment is the compound of Formula (I) wherein aryl is naphthyl. In another embodiment is the compound of Formula (I) wherein aryl is phenyl.

In yet another embodiment is the compound of Formula (I) wherein R₈ is —S(=O)₂N(R₆)₂. In a further embodiment is the compound of Formula (I) wherein R₆ is H. In yet a further embodiment is the compound of Formula (I) wherein R₆ is heteroaryl. In one embodiment is the compound of Formula (I) wherein heteroaryl is pyridine. In another embodiment is the compound of Formula (I) wherein R₈ is OH. In yet another embodiment is the compound of Formula (I) wherein q is 0. In a further embodiment is the compound of Formula (I) wherein q is 1. In yet a further embodiment is the compound of Formula (I) wherein q is 2. In one embodiment is the compound of Formula (I) wherein R₉ is OH. In another embodiment is the compound of Formula (I) wherein R₉ is —N=N-aryl. In yet another embodiment is the compound of Formula (I) wherein aryl is naphthyl. In a further embodiment is the compound of Formula (I) wherein aryl is phenyl. In yet a further embodiment is the compound of Formula (I) wherein R₉ is —S(=O)₂N(R₆)₂. In one embodiment is the compound of Formula (I) wherein R₆ is H. In another embodiment is the compound of Formula (I) wherein R₆ is heteroaryl. In yet another embodiment is the compound of Formula (I) wherein heteroaryl is pyridine. In a further embodiment is the compound of Formula (I) wherein r is 0. In yet a further embodiment is the compound of Formula (I) wherein r is 1. In one embodiment is the compound of Formula (I) wherein r is 2.

In one aspect is a compound selected from the group consisting of:

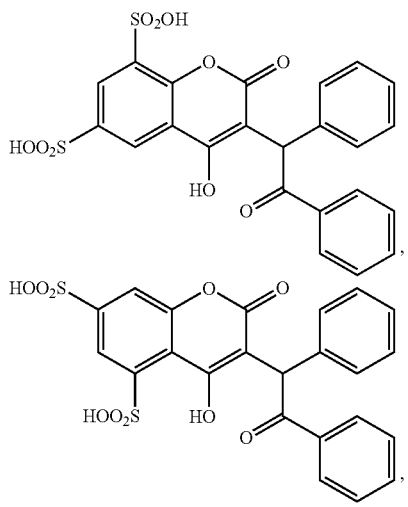

-continued
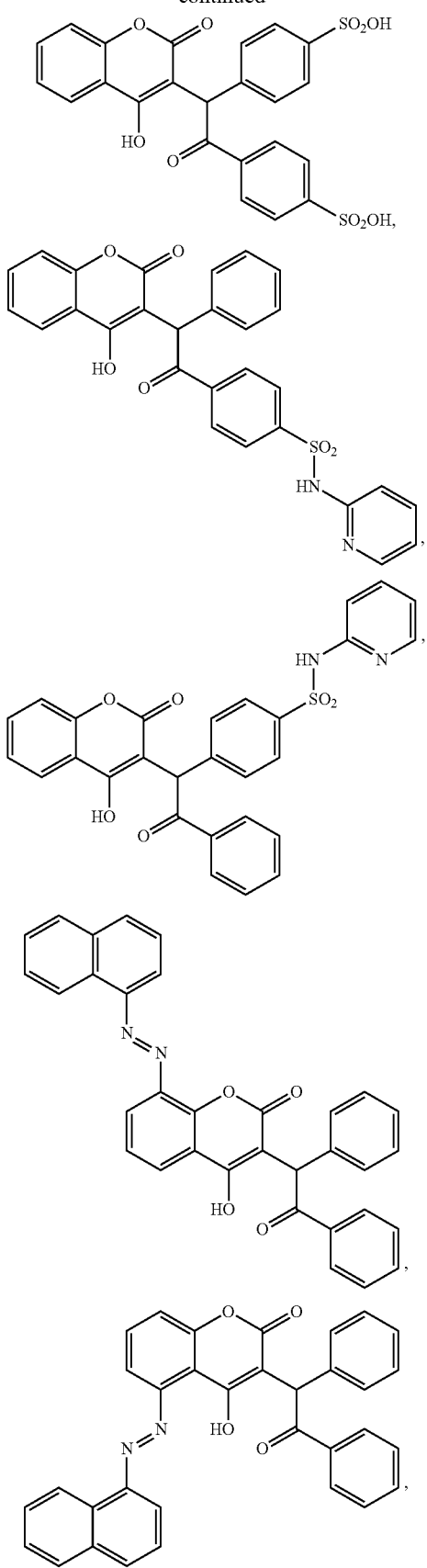
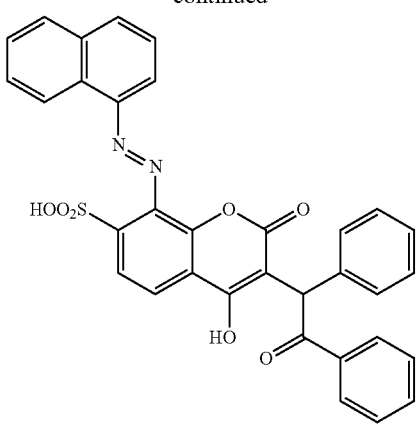
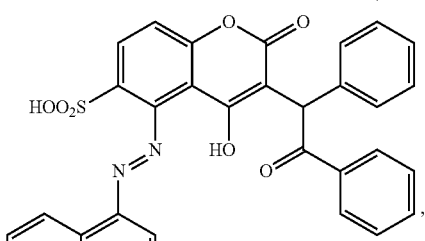
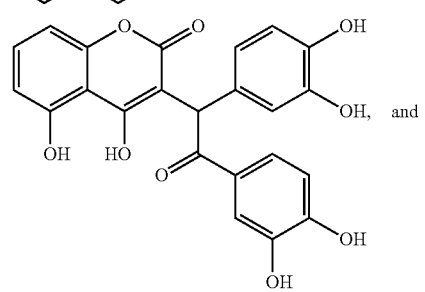
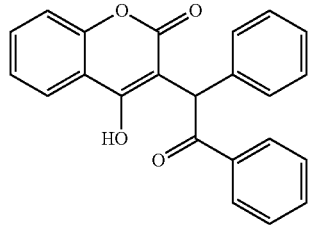 [SMILES: O=C(c1ccccc1)C(c1ccccc1)c1c(O)c2ccccc2oc1=O]
In another aspect is a compound selected from the group consisting of:
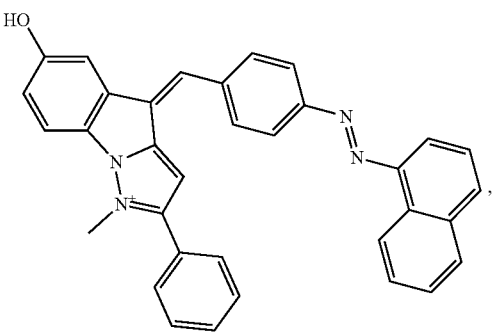

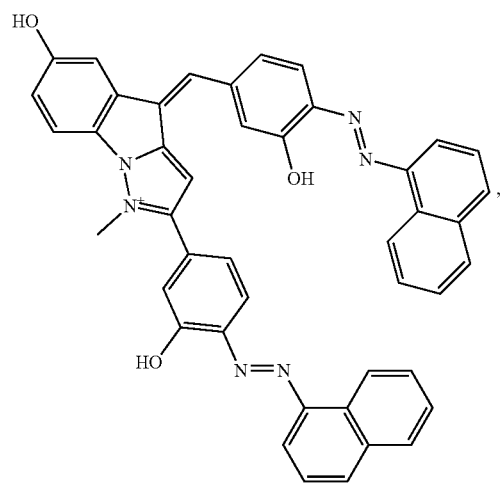
,
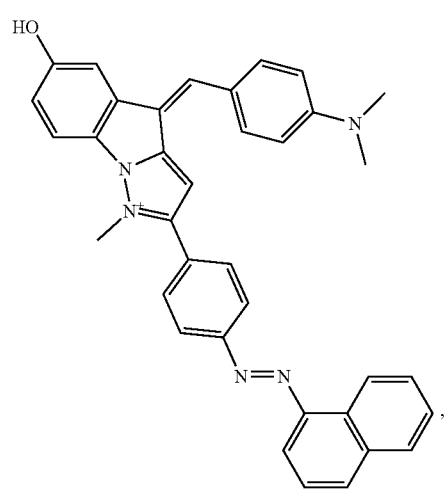
,
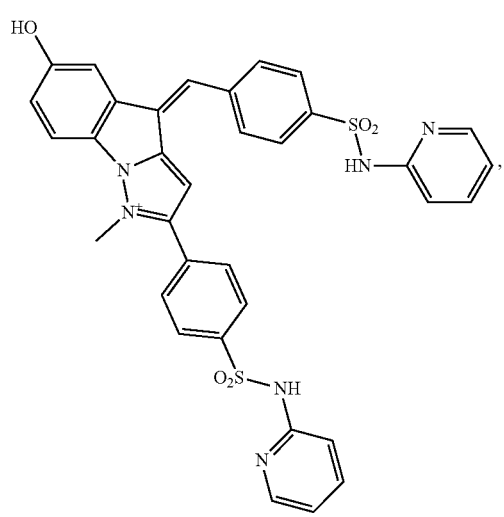
,
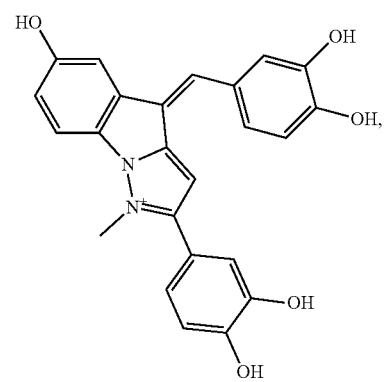
,
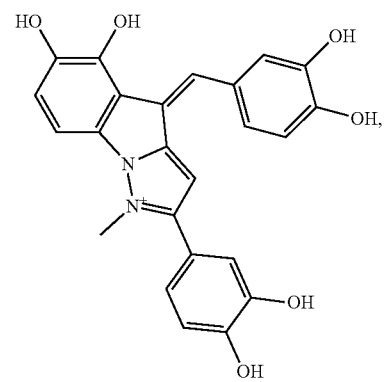
,
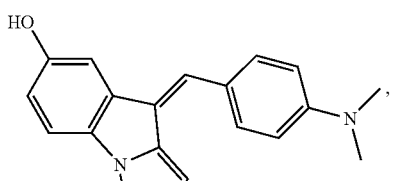
,
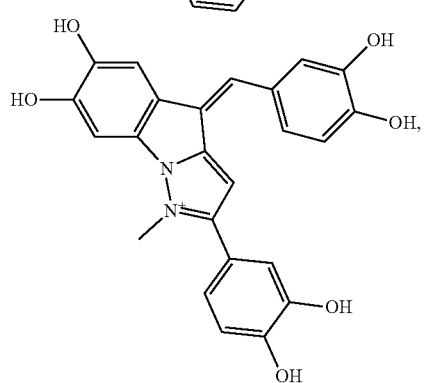
, -continued
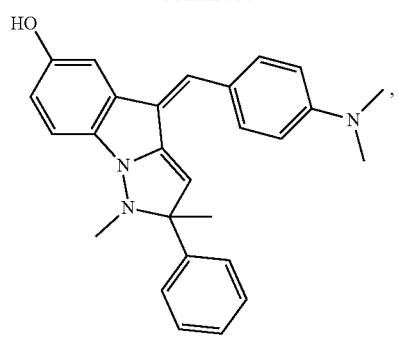
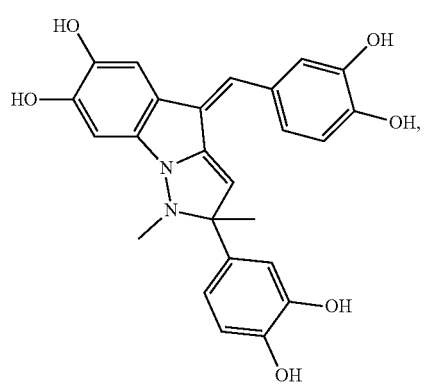
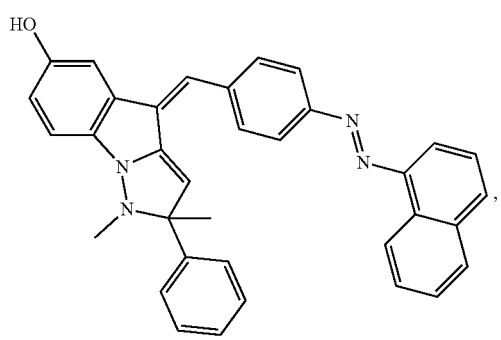
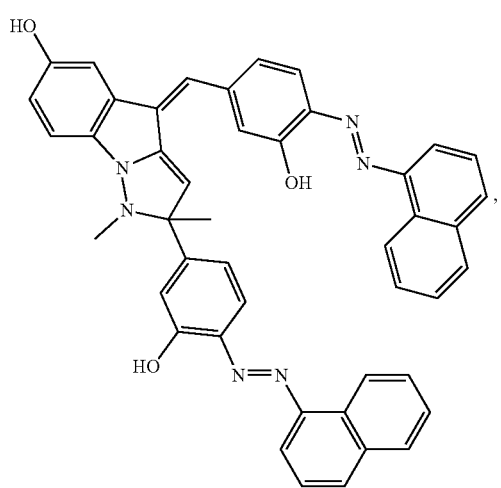
-continued
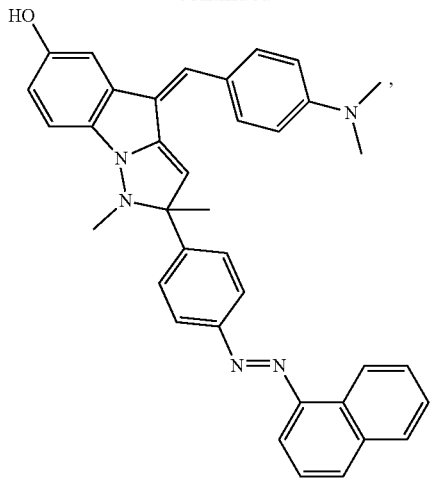
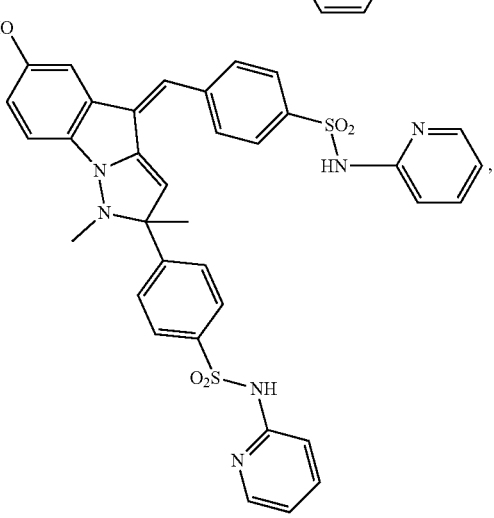
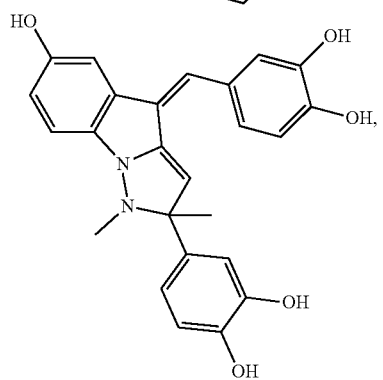
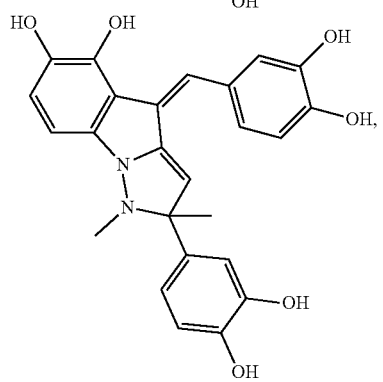

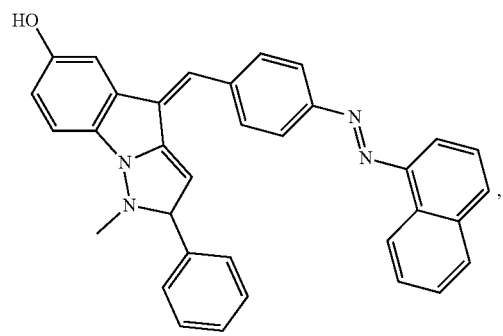
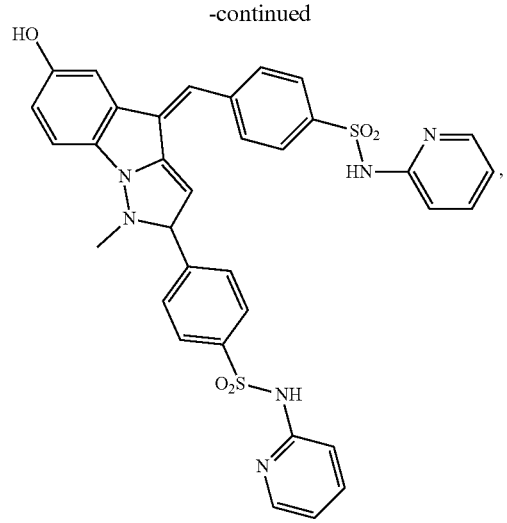
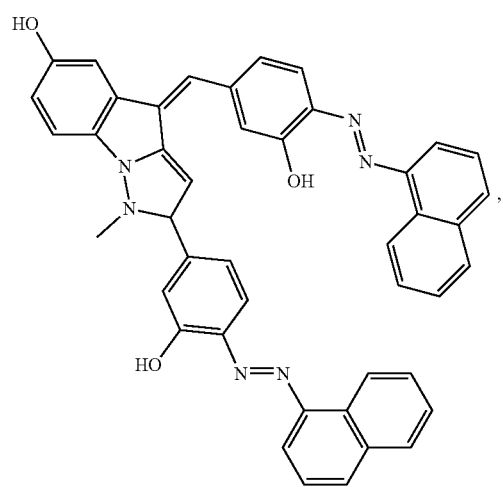
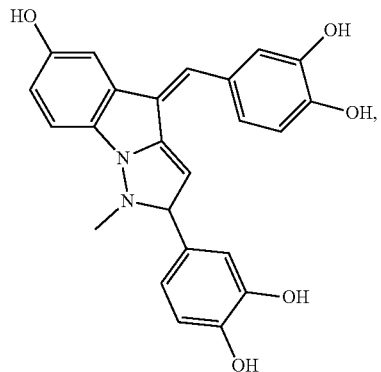
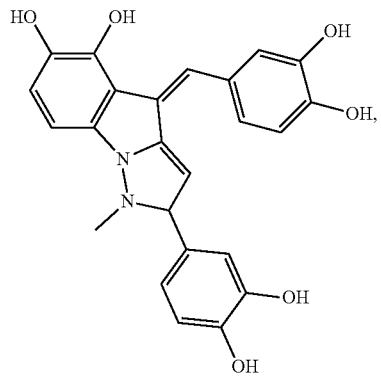
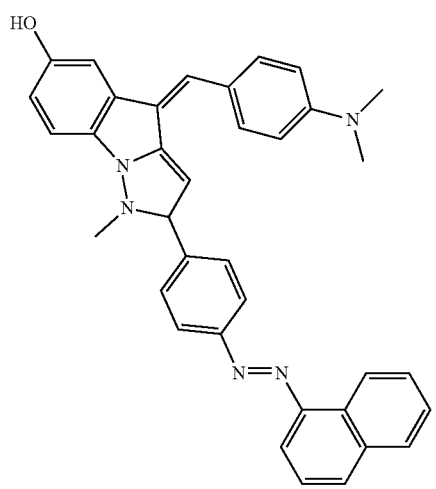
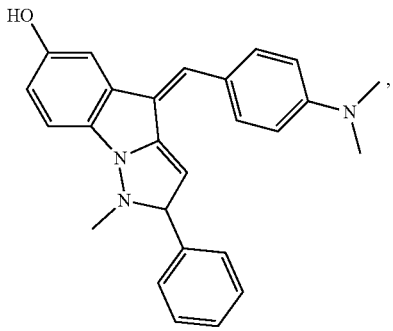

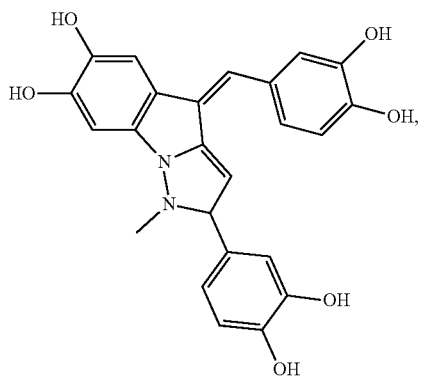
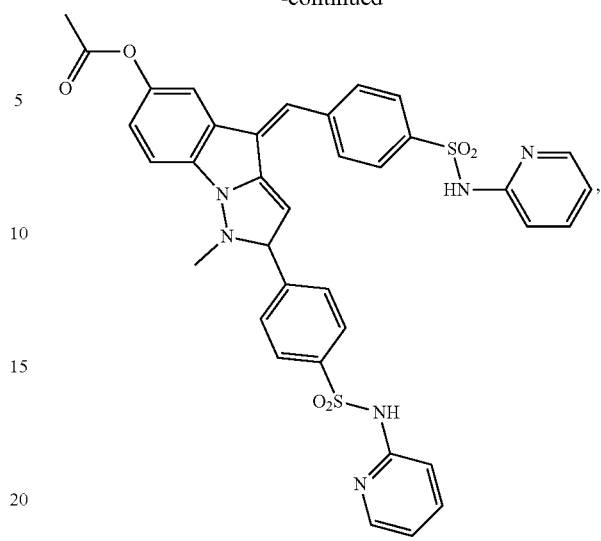
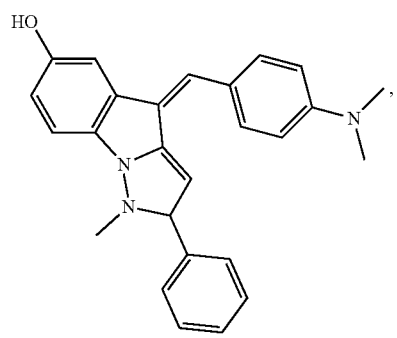
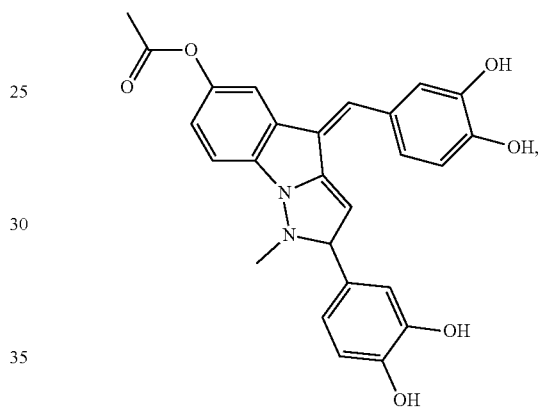
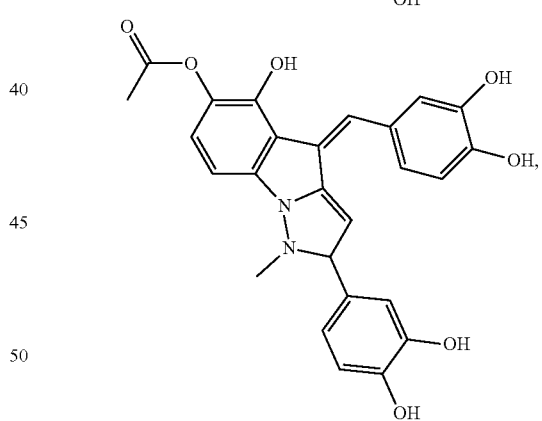
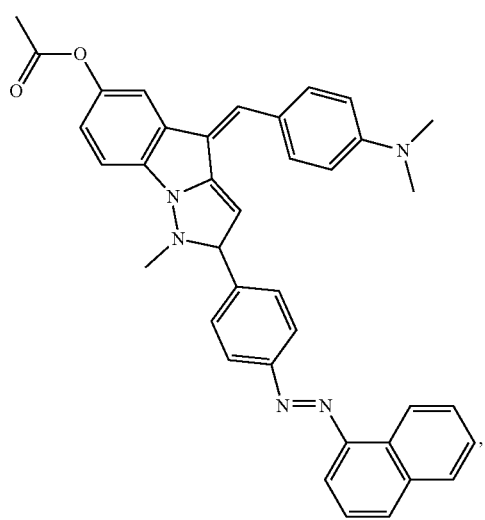
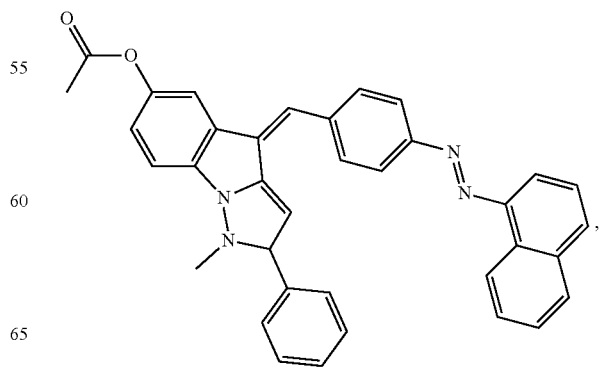

-continued

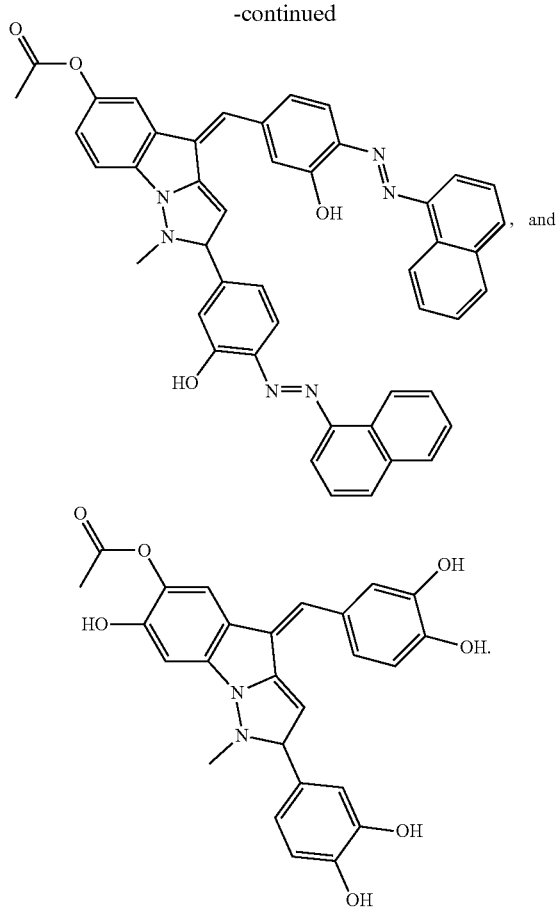

In yet another aspect is a pharmaceutical composition comprising a compound of Formula (I) or (II) or a pharmaceutically acceptable salt, solvate, prodrug or metabolite thereof and a pharmaceutically acceptable binder, excipient, or diluent thereof.

In one aspect is a method of inhibiting the growth of human prostate cancer in a subject comprising administering to a subject in need thereof an inhibitor of the JunD-AR interaction. In one embodiment, the inhibitor of the JunD-AR interaction is a compound of Formula (I) or (II).

In one aspect is a method of preventing interaction of androgen receptor with other transcription factors comprising contacting a compound of Formula (I) or (II) with an androgen receptor and/or a transcription factor wherein the interaction of androgen receptor with other transcription factors is prevented or minimized. In one embodiment the transcription factor is AP-1 transcription factor JunD.

In one aspect is a method of reducing oxidative stress and/or blocking androgen-induced oxidative stress in cancer cells and/or tissues comprising contacting the cancer cells and/or tissues with a compound of Formula (I) or (II) wherein the oxidative stress in the cancer cell and/or tissue is reduced or the androgen-induced oxidative stress in the cancer cell and/or tissue is blocked. In one embodiment the cancer cells and/or tissues is prostate cells and/or tissues. In another embodiment is a pharmaceutical composition comprising the compound of Formula (I) or (II) for the treatment of a prostate disease or disorder. In another embodiment is a pharmaceutical composition comprising the compound of Formula (I) or (II), wherein the prostate disease or disorder is inflammation of the prostate.

In one aspect is a method of inhibiting the growth of prostate cancer in a subject comprising an administration to a subject in need thereof a compound, which disrupts the function of the JunD-AR interaction and thus, blocks ROS production and prostate cancer occurrence, recurrence and progression.

In one aspect is a method of inhibiting the growth of human prostate cancer in a subject comprising administering a compound selected from:

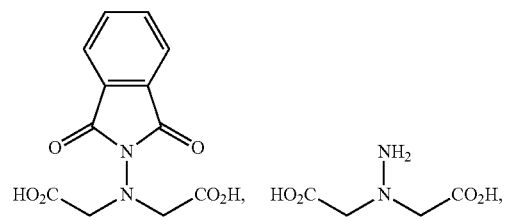

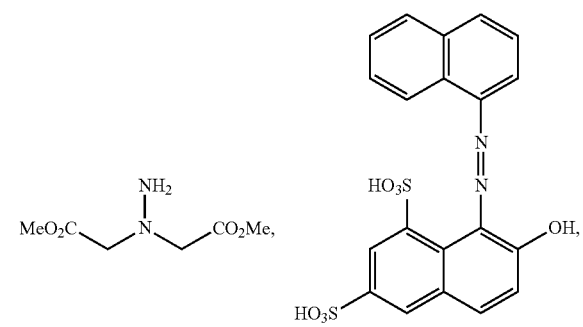

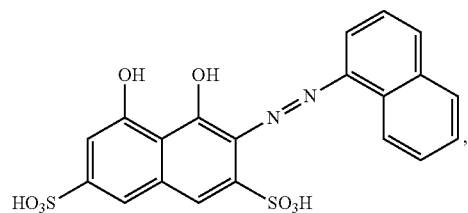

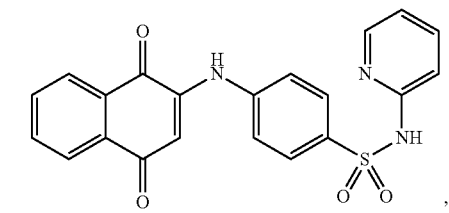

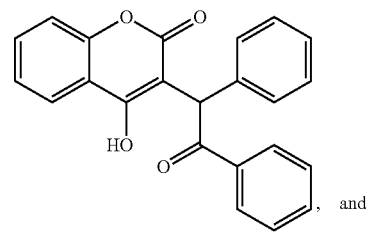

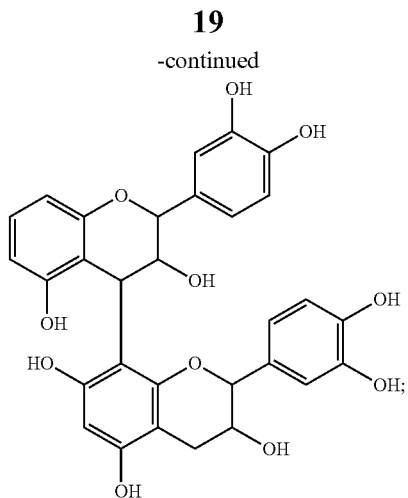

pharmaceutically acceptable salt, solvate or prodrug thereof; to a subject in need thereof; wherein the growth of human prostate cancer is inhibited.

In another aspect is a method of preventing interaction of androgen receptor with other transcription factors comprising contacting a compound selected from:

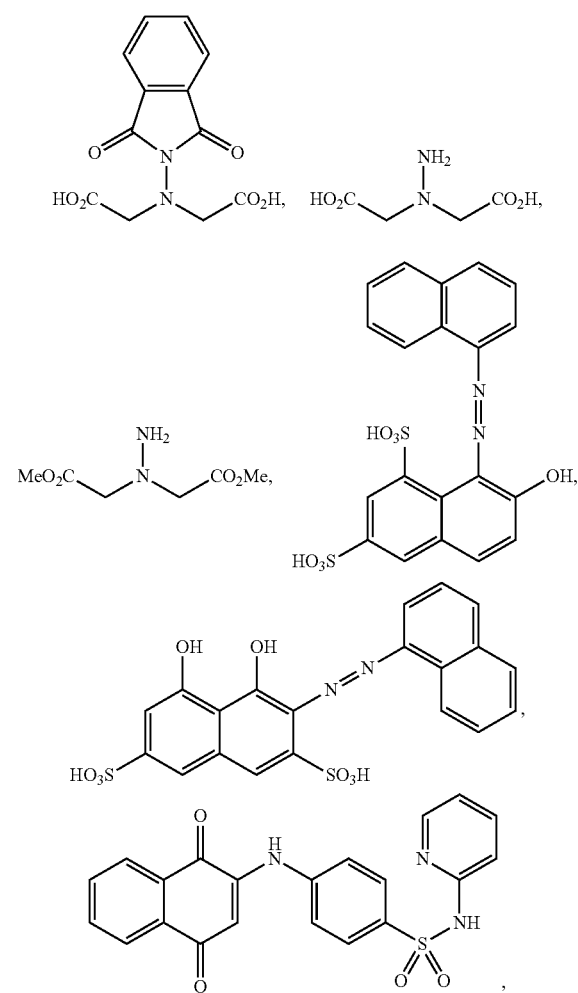

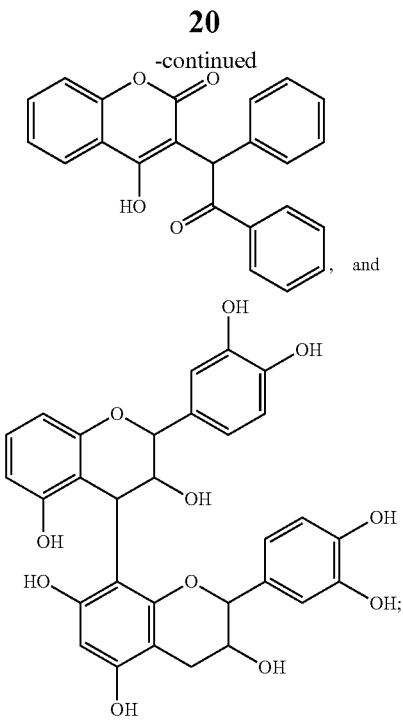

with an androgen receptor and/or a transcription factor wherein the interaction of androgen receptor with other transcription factors is prevented or minimized.

In another embodiment the transcription factor is AP-1 transcription factor JunD.

In another aspect is a method of reducing oxidative stress and/or blocking androgen-induced oxidative stress in cancer cells and/or tissues comprising contacting the cancer cells and/or tissues with a compound selected from:

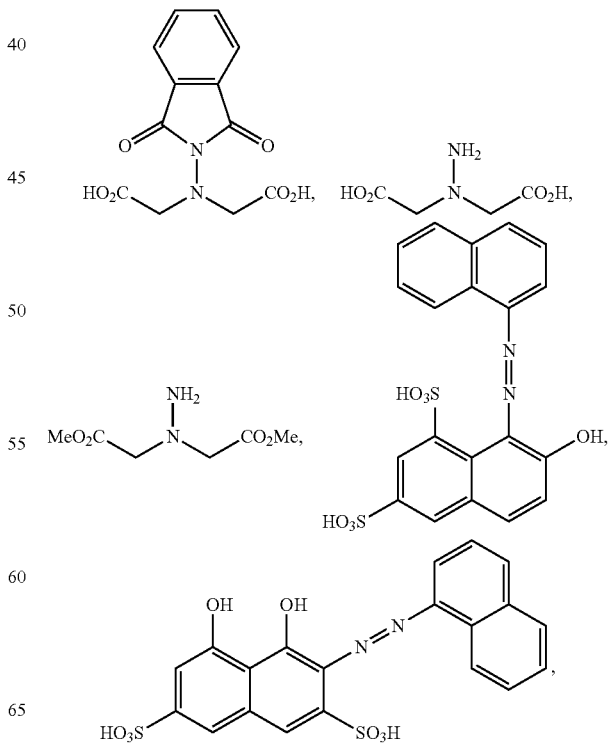

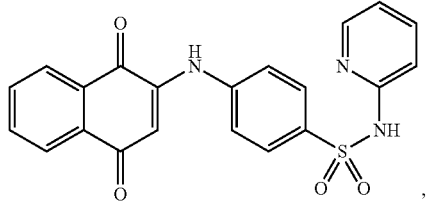

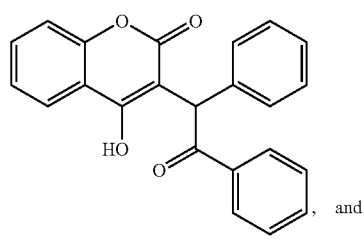, and

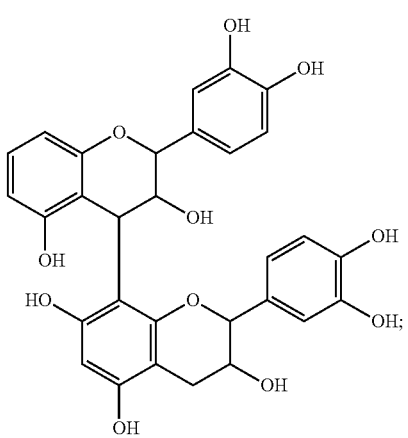

wherein the oxidative stress in the cancer cell and/or tissue is reduced or the androgen-induced oxidative stress in the cancer cell and/or tissue is blocked.

In a further embodiment is a method of reducing oxidative stress and/or blocking androgen-induced oxidative stress in cancer cells and/or tissues comprising contacting the cancer cells and/or tissues wherein the cancer cells and/or tissues are prostate cells and/or tissues.

In one aspect is a pharmaceutical composition comprising a compound selected from:

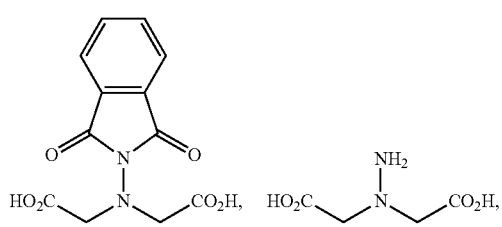

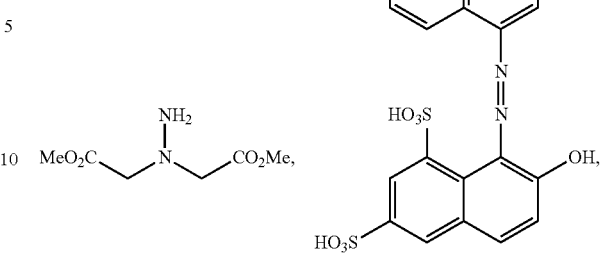

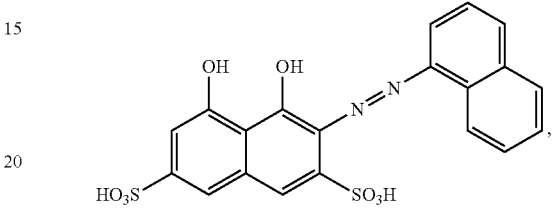

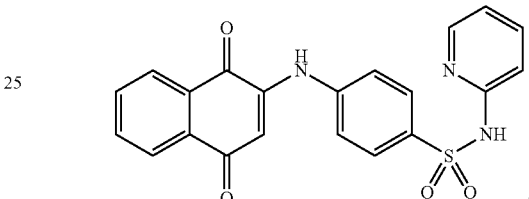

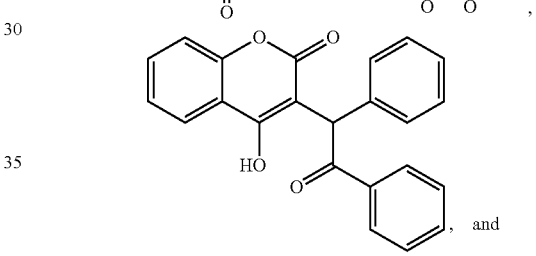, and

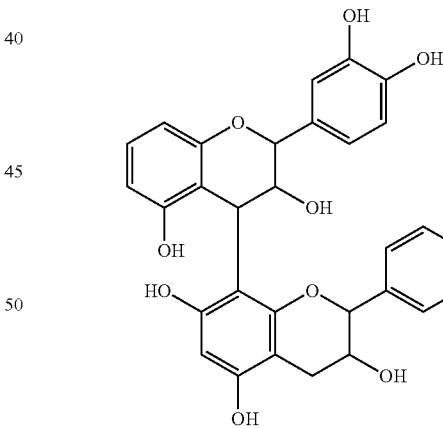

or a pharmaceutically acceptable salt, solvate, or prodrug thereof; and a pharmaceutically acceptable excipient, binder or carrier thereof.

It is understood that the examples and embodiments described above are for illustrative purposes only and that various modifications or changes in light thereof will be suggested to persons skilled in the art and are to be included within the spirit and purview of this application and scope of the appended claims.

BRIEF DESCRIPTION OF THE DRAWINGS

The accompanying drawings, which are incorporated in and constitute a part of this specification, illustrate several aspects described below. Like numbers represent the same elements throughout the figures.

FIG. 2 shows representative immunocytochemistry showing JunD translocated into LNCaP cell nuclei after androgen treatment. LNCaP cells were untreated (−R1881) (A) or treated with androgen (1 nM R1881) (B) for 72 h, then fixed, stained with JunD primary-AlexaFluor594 secondary antibody pair, and observed using an Olympus microscope model Mercury 100 fluorescence. (100×-magnification). Nuclei were identified by DAPI staining (data not shown). The experiment was repeated 2 times, including 6 slides in 2 replicates per condition with similar results.

FIG. 5 shows Chromatin ImmunoPrecipitation (ChiP) assay identifying a binding site for JunD but not AR within the SSAT promoter sequence: ChiP assay studies were carried out in LNCaP cells treated with androgen (lnM R1881) using primer pairs targeted to identify the SSAT promoter sequence (see text). A. Agarose gel electrophoresis of PCR products showing the only PCR product obtained, which was from DNA fragments immunoprecipitated by JunD antibody (Lane:JunD) using the F1R1 primer pair. Using the same F1R1 primer pair, no PCR product was obtained from immunoprecipitation of chromatin fragments by AR antibody (Lane:AR), nor from the non-specific IgG (Lane:IgG) controls. M: DNA Ladder size marker. B. Sequence of the PCR product, which was cloned into PCR2.1TOPO and sequenced using M13 primer, matches −574 to −651 bp of the SSAT gene promoter (SEQ ID NO: 1; NCBI accession #1103903).

FIG. 13 shows a graphical representation of the polarization assay that test a compounds ability to bind the androgen receptor-LBD. In FIG. 13a bicalutamide displays the antiandrogen profile. In FIG. 13b compound 81 showed a classical antiandrogen curve. In FIG. 13c compound 71 and in FIG. 13d compound 31 did not show an antiandrogen profile and therefore were classified as non-antiandrogens.

FIGS. 14a and 14b show the structure and classification of all compounds into non-antiandrogens and antiandrogens from the Polarization assay.

FIG. 18 shows the LC-MS profile of 1 ng of compound 71 extracted from spiked mouse serum.

DETAILED DESCRIPTION

Figure 1:
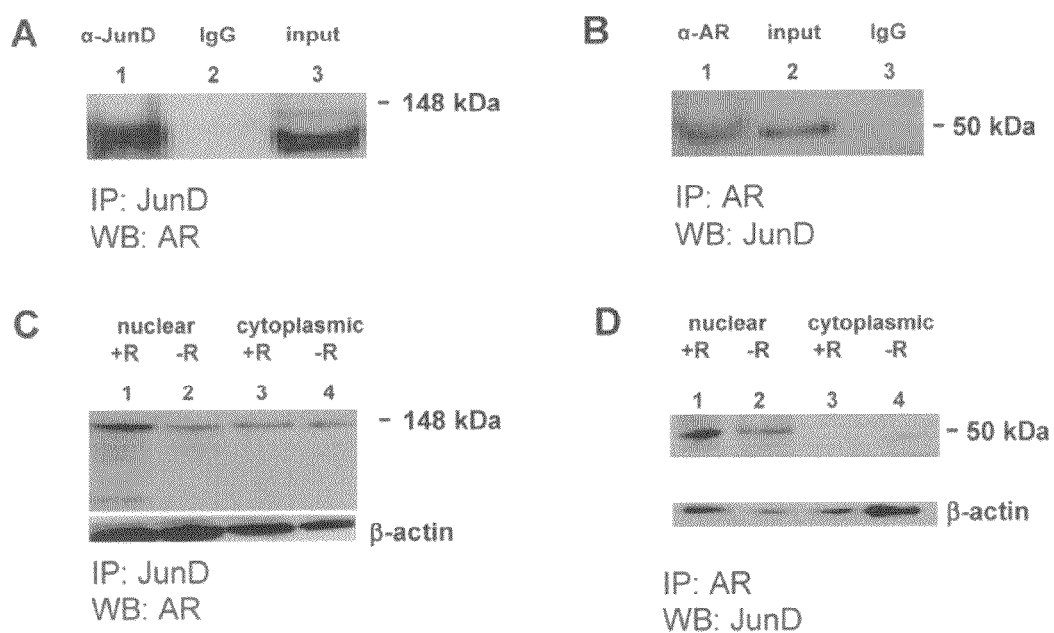
FIG. 1 shows representative Western blots showing JunD and Androgen Receptor (AR) in an immunocomplex in LNCaP cell lysates: A. Immunoprecipitation (IP) of LNCaP whole cell lysate was performed using a rabbit polyclonal antibody against JunD (sc-74X) (IP:JunD). Immunoprecipitates were analyzed by western blot (WB) using monoclonal antibody against human AR (sc-7305) (WB:AR). Lane (1): IP with JunD antibody, Lane (2): IP with non-specific IgG, Lane (3): total LNCaP cell lysate. B. IP of LNCaP whole cell lysate was performed using AR antibody (sc-7305) (IP:AR) and WB analysis using JunD antibody (sc-74X) (WB:JunD). Lane (1): IP with AR antibody, Lane (2): total LNCaP cell lysate, Lane (3): IP with non-specific IgG. Positions of molecular size markers 148 kDa (A) and 50 kDa (B) are shown on the right. The experiment was repeated 3 times with similar results. C. IP:JunD/WB:AR of LNCaP nuclear and cytoplasmic extracts was performed as described in (A) above. Lane (1): nuclei from cells treated with R1881 (+R), Lane (2): nuclei from untreated (—R) cells, Lane (3): cytoplasm from cells treated with R1881 and Lane (4): cytoplasm from untreated cells. D. IP:AR/WB:JunD of LNCaP nuclear and cytoplasmic extracts was performed as described in (B) above. Lane (1): nuclei from cells treated with R1881 (+R), Lane (2): nuclei from untreated (—R) cells, Lane (3): cytoplasm from cells treated with R1881 and Lane (4): cytoplasm from untreated cells.

Androgen signaling is one source of ROS generation in prostatic epithelial cells. Androgen binding to androgen receptor (AR) initiates a cascade of events leading to ROS generation in prostate cells. One pathway of androgen-induced oxidative stress involves activation of AP-1 transcription factor, JunD, followed by induction of the enzyme known as spermidine/spermine N1-acetyl transferase (SSAT) that initiates a major spermidine and spermine oxidation pathway. As prostatic epithelia produce a large excess of spermine and spermidine, induction of their oxidation could result in high ROS levels in the prostate.

Advanced castration-resistant prostate cancer (CRPCa) is the second leading cause of cancer deaths among US men. Most conventional cancer therapies are only modestly effective against CRPCa.

Described herein are compositions and methods to prevent, treat or cure PCa recurrence and progression by natural cancer causative agents, including cellular reactive oxygen species (ROS), such as superoxide, hydroxyl radical, hydrogen peroxide, etc. In human PCa cells, excess cellular ROS activate the transcription factor NF-κB that sets up an autocrine feed-forward-loop to keep NF-κB active, which prevents apoptosis and drives PCa cell proliferation in the absence of androgen. The targeted drugs described herein are inhibitors of PCa specific ROS generation pathway(s) and are more effective than are certain dietary anti-oxidants in preventing PCa recurrence and progression to CRPCa. Androgen induces SSAT that initiates a spermidine and spermine oxidation pathway generating copious amounts of ROS in polyamine-rich prostate cells. JunD protein expression is induced by androgen specifically in PCa cells and JunD complexes with the activated androgen receptor (AR) to induce SSAT gene expression in these cells. In one embodiment is a chemical entity inhibitor(s) of the JunD-AR complex, which block ROS production, NF-κB activation and prevent CRPCa proliferation. We used a *Gaussia* luciferase enzyme reconstitution assay for in situ protein-protein interaction in a high throughput screen to identify JunD-AR interaction inhibitors.

Several compounds significantly inhibiting the JunD-AR interaction are described herein. At least two of these compounds blocked androgen-induced ROS generation in androgen-dependent PCa cells and showed growth inhibitory effects against both androgen-dependent and androgen-independent human PCa cells. Also described herein are data showing selected small molecules inhibit JunD-AR interaction. Also described herein is the synthesis of these molecules and identified chemo-preventative and chemo-therapeutic agents with abilities to disrupt JunD-AR interaction and as drug formulations efficacious in reducing ROS and inhibit human PCa cell and tumor growth. Also disclosed herein are compounds which inhibit human PCa growth in vivo.

Androgen activation of AR in LNCaP human PCa cells induces the AP-1 transcription factors Fra-2 and JunD. However, only JunD levels and its functional activity remain elevated for 96 h after androgen treatment, when androgen-induced ROS production is observed. Without being bound by a particular theory, it is thought that JunD either inhibits or helps cellular ROS production, depending on the cell type, presence of ROS-generating proteins, growth conditions, etc. Since androgen-induced ROS generation is abrogated by either blocking androgen-induced JunD overexpression with anti-androgen bicalutamide, or by silencing JunD protein expression using siRNA, and it is concluded that JunD activity is necessary for androgen-induced oxidative stress in PCa cells.

While androgens produce oxidative stress in prostate cells that plays a key role in the occurrence and progression of PCa, the exact molecular mechanism of androgen-induced oxidative stress generation in prostatic epithelia and prostate cancer cells has only recently being elucidated. We showed that AP-1 transcription factor JunD plays a key role in androgen induction of ROS. Further, we have shown that androgen significantly induces the expression and enzymatic activity of SSAT, a regulatory enzyme in the spermidine and spermine catabolic pathway that produces a large excess of ROS in spermidine and spermine-rich prostate cells. Described herein is a relationship at the molecular level between these two components that establishes the mechanism of androgen-induced ROS generation in prostate cells.

The binding sites of many important transcription factors in the SSAT gene promoter have been identified. Because the SSAT gene promoter sequence lacks an AR binding site (ARE), the mechanism of androgen-induced SSAT expression was unclear. Described herein is a direct binding of androgen-activated AR with JunD, binding of JunD with the SSAT promoter, and that an induction of SSAT by androgen which occurs following the interaction of JunD with a specific sequence in the SSAT promoter only in androgen treated LNCaP cell chromosome, most probably due to the formation of an activated AR-JunD complex.

Androgen-activated AR induces over-expression of the transcription factor JunD, as well as activating JunD binding to the AP-1 DNA-binding sequence in LNCaP cells. Described herein is an androgen treatment, which causes AR and JunD to co-precipitate as an immunocomplex from LNCaP cell lysates. Relatively more complex precipitates from the nuclear fraction than from the cytoplasmic fraction (FIG. 1). Androgen treatment induces translocation of JunD into the nucleus in LNCaP cells (FIG. 2) at the same time as AR translocates into the nucleus, as shown by immunoprecipitation/western blotting of nuclear extracts (FIG. 1C). These observations show an interaction of activated AR with JunD in androgen-treated PCa cells that also causes functional activation of JunD.

Figure 3:
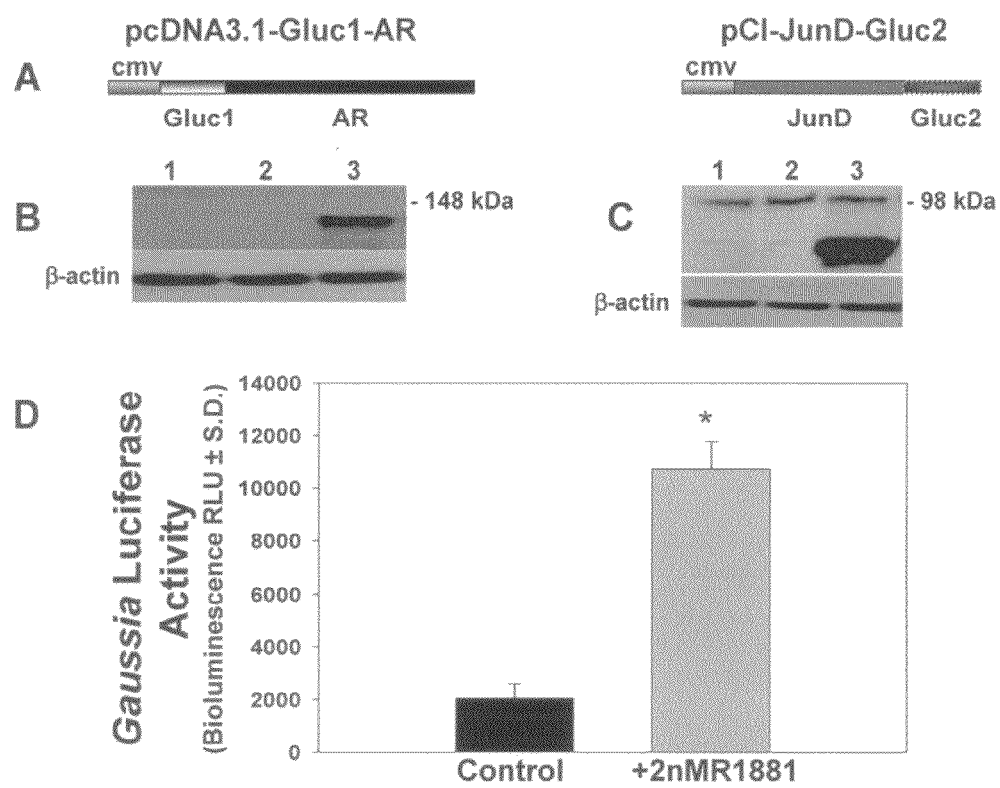
FIG. 3 shows Western blot and bioluminescence analysis demonstrating expression of Gluc1-AR and JunD-Gluc2 and reconstitution of *Gaussia* luciferase activity following androgen stimulation in transfected Hep3B cells: A Schematic diagrams for Gluc1-AR and JunD-Gluc2 fusion constructs. B. Representative Western blot of Hep3B cell lysates analyzed using AR antibody. Lane (1): Hep3B cells transfected with control vector (pcDNA3.1); Lane (2): control untransfected Hep3B cells; Lane (3): Hep3B cells transfected with Gluc1-AR. C. Representative Western blot of Hep3B cell lysates analyzed using *Gaussia* luciferase antibody. Lane (1): Hep3B cells transfected with control vector (pCI); Lane (2): control untransfected Hep3B cells; Lane (3): Hep3B cells transfected with JunD-Gluc2. Membranes were stripped and probed with monoclonal antibody against β-actin to control for protein loading (B,C). Positions of molecular size markers 148 kDa (B) and 98 kDa (C) are shown on the right. Cell lysates were obtained and analyzed by western blot from six independent transfection experiments for each construct with similar results. D. *Gaussia* luciferase activity in co-transfected cells: Hep3B cells were co-transfected with Gluc1-AR and JunD-Gluc2, then treated with androgen (2 nM R1881) (gray bar) or left untreated (−R1881) (black bar). Cell lysates were collected after 48 h and bioluminescence activity of *Gaussia* luciferase was assayed by measuring light emitted from reconstituted Gluc1-Gluc2 at 480 nm. Reconstitution of Gluc1-Gluc2 and resulting *Gaussia* luciferase activity was significantly increased >5-fold in androgen treated cells compared to untreated control cells. Lysates used for these studies were collected from six independent transfections each run in triplicate. * $P<10^{-8}$.

Additional direct evidence of AR and JunD interaction was demonstrated using the *Gaussia* luciferase reconstitution assay which has been standardized to study in situ protein-protein interactions. The significant reconstitution of *Gaussia* luciferase activity only in androgen-treated Hep3B cells transfected with vectors expressing N-terminal and C-terminal fragments of Gaussia luciferase enzyme linked to AR and JunD, respectively, provides evidence of JunD interaction with androgen-activated AR in situ (FIG. 3D). While immunoprecipitation and co-localization of AR with another AP-1 family member, c-Jun, has been reported, to the best of our knowledge, this is the first direct demonstration of androgen-activated AR and JunD complex formation.

Since overexpression of JunD is necessary for the induction of ROS following androgen exposure, in some embodiments, the AR-JunD complex regulates expression of genes involved in ROS production in LNCaP cells. In further embodiments, the complex binds via JunD to sequences containing binding sites for members of the AP1 family of transcription factors (TGA$^{G/C}$TCA)). These sequences may or may not contain any ARE sequences. Thus, many genes such as SSAT that are not directly regulated by AR might be regulated by an AR-JunD complex.

Figure 4:
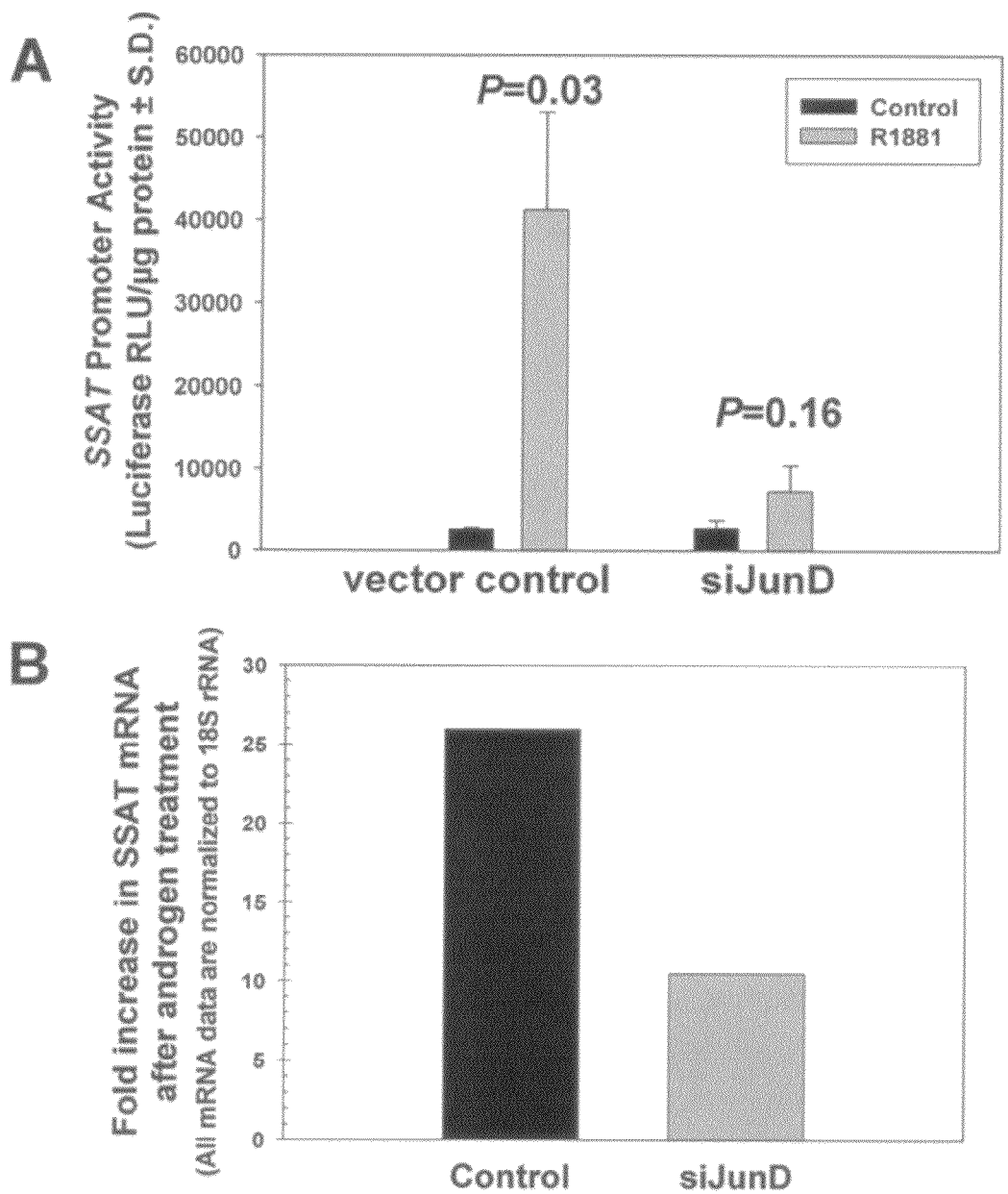
FIG. 4 shows androgen-induced increase in SSAT promoter activity is abrogated when JunD is silenced in LNCaP cells. A. LNCaP cells in which JunD is silenced (siJunD) and respective vector control LNCaP cells were transiently transfected with an SSAT promoter luciferase reporter vector, then treated with androgen (1 nM R1881) (gray bars) or left untreated (Control) (black bars). Cell lysates were collected after 72 h and firefly luciferase activity was measured. Data and error bars are respectively the mean and standard deviation from 18 data points of measured relative light units (RLU) normalized to protein concentration from 6 independent repeat transfection/treatment experiments (n=3 samples per condition for each experiment). P-values were calculated using a two-tailed Student's t-test assuming unequal variance. B. SSAT mRNA levels as determined by qRT-PCR showing a >25-fold increase in SSAT mRNA in vector control cells and only 10-fold increase in SSAT mRNA in JunD silenced cells (siJunD). Results are presented as a ratio of mRNA in androgen-treated/androgen-untreated cells after normalizing for corresponding 18rRNA. Data are mean of three independent observations.

Described herein, by scanning the SSAT gene promoter sequence in silico, is the identification of six putative API binding sites. Further, by using our siJunD clone of the LNCaP cell line, it has been shown that in the absence of JunD, androgen-activated AR does not induce SSAT expression (FIG. 4). In other embodiments, androgen activated AR requires JunD for SSAT expression.

A direct binding of JunD to the SSAT promoter sequence was demonstrated by the Chromatin ImmunoPrecipitation (ChIP) assay (FIG. 5). By PCR analysis with primers designed to identify the SSAT promoter, we obtained a PCR product that corresponds to a DNA fragment of the SSAT promoter only in the chromatin fragment precipitated by JunD antibody and not in the chromatin fragment precipitated by AR antibody only in androgen-treated LNCaP cell nuclear extract (FIG. 5A). This shows that under these conditions, where JunD directly binds to the −574 bp to −651 bp of the SSAT promoter, there may not be a direct binding of AR to the SSAT promoter. Further elucidation of this mechanism also explains the delay in SSAT expression and ROS generation (72 h) after androgen treatment, as previously reported.

Figure 6:
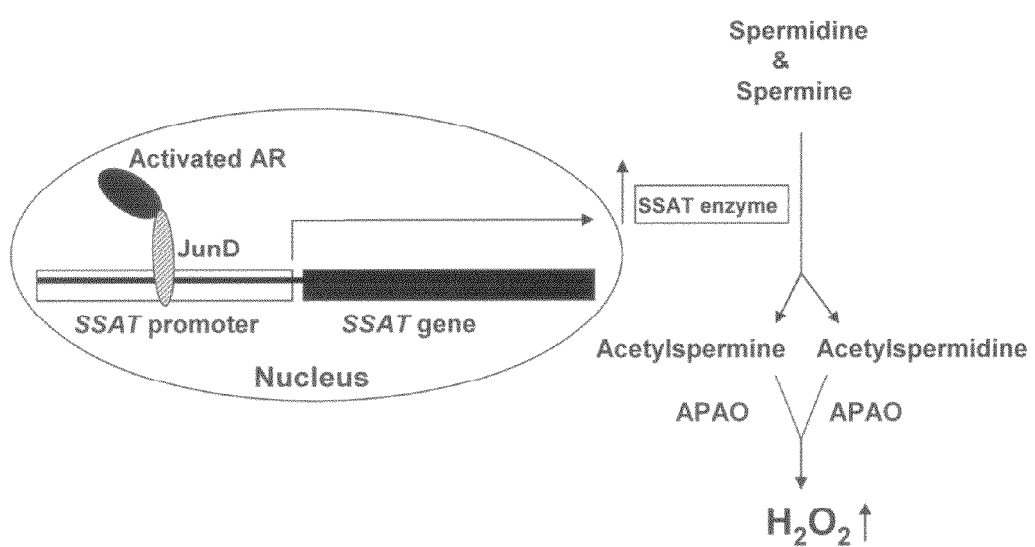
FIG. 6 shows schematic diagram showing a possible mechanism of androgen-induced increase in cellular ROS production in CaP cells through an AR-JunD complex. APAO:N'-acetylpolyamine oxidase; $H_2O_2$:hydrogen peroxide.

Collectively, our data show that activated AR forms a complex with JunD that binds to an AP-1 DNA-binding sequence in the SSAT promoter to activate SSAT gene transcription, resulting in over-production of $H_2O_2$ in PCa cells, as shown in FIG. 6. Provided herein is a molecular mechanism of androgen-induced increase in SSAT activity and consequent ROS over-production in CaP cells. The demonstration of a mechanistic pathway of androgen-induced ROS production opened up a new avenue for development of drugs that specifically target steps in this ROS generating pathway in CaP cells and thus drugs that can be effective in therapy and/or prevention of CaP without major systemic toxicity.

Described herein are methods of inhibiting androgen-induced ROS production using different small molecule inhibitors of the androgen signaling pathway or polyamine oxidation which in some embodiments also inhibits cell growth and androgen-induced ROS generation in cultured human PCa cells. Also described herein are PCa chemopreventive agents that in some embodiments specifically block this pathway. In other embodiments, the elucidation of the mechanism of androgen-induced SSAT gene expression is also described herein as an approach to identify inhibitors of androgen-induced ROS production.

Reducing ROS inhibits androgen-independent growth of androgen-dependent PCa cells. In some embodiments, agents that specifically block metabolic ROS generation in PCa cells should be better than dietary or chemical anti-oxidants that can be readily oxidized in cells producing metabolic ROS.

Androgens induce ROS production in PCa cells. We have identified that in PCa cells, androgen induces overproduction of an AP-1 transcription factor JunD and also induces marked upregulation of SSAT. SSAT is the first enzyme in a spermidine and spermine catabolic pathway that produces copious amounts of ROS in PCa cells that have 500-1,000 fold higher levels of polyamines as compared to any other tissue.

Transcription Factor JunD.

JunD is a redox-sensitive transcription factor. JunD is responsible for the transcription of a diverse array of genes with conflicting functions based on the tissue type.

JunD in PCa Cells.

In androgen-dependent LNCaP cells, it has been observed that 96 hour androgen exposure that induces high oxidative stress also increases JunD protein level, DNA binding and transcriptional activity. An anti-androgen, bicalutamide, completely attenuates these effects, implying that JunD function is mediated though an activated AR. Also provided herein is the silencing of JunD expression using siRNA abrogates androgen-induced ROS production in LNCaP cells. These data suggest that in PCa cells, JunD is one of the key players in the androgen-induced ROS generation pathway.

Spermidine and Spermine Metabolism.

The polyamines putrescine, spermidine and spermine are organic cations that are present in all mammalian cells. Since the discovery of spermine by Leeuwenhoek in human seminal fluid in the mid $17^{th}$ century, it was documented that the prostate gland is a uniquely rich factory of polyamine production. The semen of healthy men contains a large amount of spermine (~3 mM) that originates mainly from prostatic secretion.

SSAT and ROS Production.

Figure 7A:
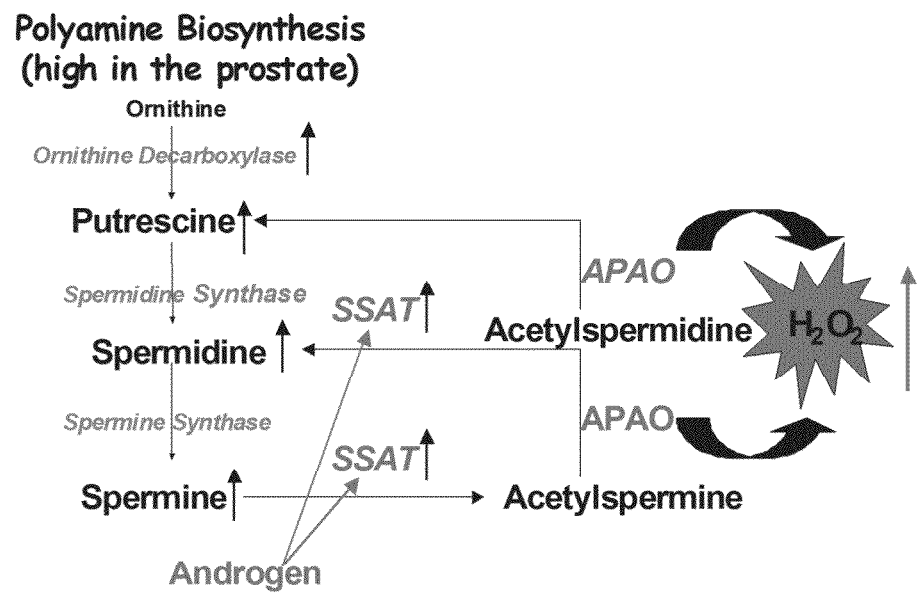
FIG. 7a shows androgen induced SSAT induction in prostate cells causes spermidine/spermine oxidation and ROS production.

The polyamine metabolic pathway is shown in FIG. 7a. The first and the rate-limiting enzyme in polyamine catabolism is spermidine/spermine $N^1$-acetyltransferase (SSAT) that produces N-acetyl polyamines. These, in turn, are oxidized by the constitutive enzyme acetyl polyamine oxidase (APAO), which is a FAD containing enzyme that recycles by producing $H_2O_2$. Our data demonstrate that androgen induces an over 20-fold upregulation of SSAT mRNA followed by an increase in SSAT enzyme activity in LNCaP cells. Because of the unusually high spermidine and spermine levels in prostate cells, SSAT induction causes a large increase in ROS production (FIG. 7a) and is likely to be one of the major causes of the androgen-induced ROS production in CaP cells. In some embodiments, blocking this pathway prevents PCa occurrence and progression.

Compounds

Described herein are compounds which disrupt JunD-AR interactions having the structure of Formula (I) or (II).

In one aspect is a compound of Formula (I):

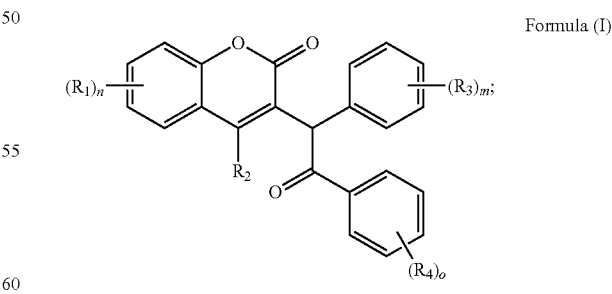

Formula (I)

wherein:

$R_1$, $R_3$ and $R_4$ are each independently selected from H, D, F, Cl, Br, I, —CN, —NO$_2$, —OH, —CF$_3$, —OCF$_3$, —OR$_4$, —NR$_6$R$_6$, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, optionally substituted aryl, optionally substituted O-aryl, optionally substituted heteroaryl, —N=N-aryl, —NHS(=O)$_2$R$_5$, —S(=O)$_2$N(R$_6$)$_2$, —N(R$_6$)S(=O)$_2$N(R$_6$)$_2$, —C(=O)CF$_3$, —C(=O)NHS(=O)$_2$R$_5$, —S(=O)$_2$NHC(=O)R$_5$, —N(R$_6$)$_2$, —N(R$_6$)C(=O)R$_6$, —N(R$_6$)C(=O)N(R$_6$)$_2$, —N(R$_6$)C(=O)OR$_5$, —CO$_2$R$_6$, —C(=O)R$_6$, —OC(=O)R$_5$, —OC(=O)N(R$_6$)$_2$, —CON(R$_6$)$_2$, —SR$_6$, —S(=O)R$_5$, and —S(=O)$_2$R$_5$;

each R$_5$ is independently selected from C$_1$-C$_6$alkyl, C$_1$-C$_6$haloalkyl, C$_3$-C$_8$cycloalkyl, aryl, and benzyl;

each R$_6$ is independently selected from H, C$_1$-C$_6$alkyl, C$_1$-C$_6$haloalkyl, C$_3$-C$_8$cycloalkyl, aryl, and benzyl;

R$_2$ is selected from H, OH, OC(=O)C$_1$-C$_6$alkyl, or OC(=O)H;

n is an integer selected from 0-4;

m and o are each independently an integer selected from 0-5;

or a pharmaceutically acceptable salt, solvate, prodrug or metabolite thereof.

In another aspect is a compound of Formula (II) or (III):

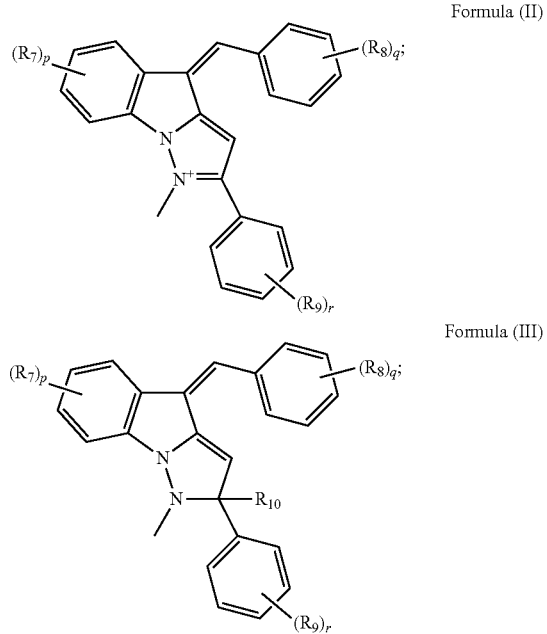

Formula (II)

Formula (III)

wherein:

R$_7$, R$_8$ and R$_9$ are each independently selected from H, D, F, Cl, Br, I, —CN, —NO$_2$, —OH, —CF$_3$, —OCF$_3$, —OR$_4$, —NR$_6$R$_6$, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, optionally substituted aryl, optionally substituted O-aryl, optionally substituted heteroaryl, —N=N-aryl, —NHS(=O)$_2$R$_5$, —S(=O)$_2$N(R$_6$)$_2$, —N(R$_6$)S(=O)$_2$N(R$_6$)$_2$, —C(=O)CF$_3$, —C(=O)NHS(=O)$_2$R$_5$, —S(=O)$_2$NHC(=O)R$_5$, —N(R$_6$)$_2$, —N(R$_6$)C(=O)R$_6$, —N(R$_6$)C(=O)N(R$_6$)$_2$, —N(R$_6$)C(=O)OR$_5$, —CO$_2$R$_6$, —C(=O)R$_6$, —OC(=O)R$_5$, —OC(=O)N(R$_6$)$_2$, —CON(R$_6$)$_2$, —SR$_6$, —S(=O)R$_5$, and —S(=O)$_2$R$_5$;

each R$_5$ is independently selected from C$_1$-C$_6$alkyl, C$_1$-C$_6$haloalkyl, C$_3$-C$_8$cycloalkyl, aryl, and benzyl;

each R$_6$ is independently selected from H, C$_1$-C$_6$alkyl, C$_1$-C$_6$haloalkyl, C$_3$-C$_8$cycloalkyl, aryl, and benzyl;

R$_{10}$ is H or C$_1$-C$_6$alkyl;

p is an integer selected from 0-4;

q and r are each independently an integer selected from 0-5; or a pharmaceutically acceptable salt, solvate, prodrug or metabolite thereof.

Polyamine Oxidase Inhibitor as a CaP Chemopreventive/Chemotherapeutic Drug.

Described herein are molecules, such as for example, N,N'-butadienyl-butanediamine inhibitor of APAO or one of its pro-drugs or analogs, as shown in the figures disclosed herein in this application. Pretreatment with N,N'-butadienyl-butanediamine completely blocks androgen-induced ROS production in human CaP cells. N,N'-butadienyl-butanediamine treatment also markedly reduces oxidative stress in the prostate of TRansgenic Adenocarcinoma in Mouse Prostate (TRAMP) animals and significantly prevents CaP progression in these animals. SSAT promoter sequence, however, contains no AR-binding element (ARE).

Figure 7B:
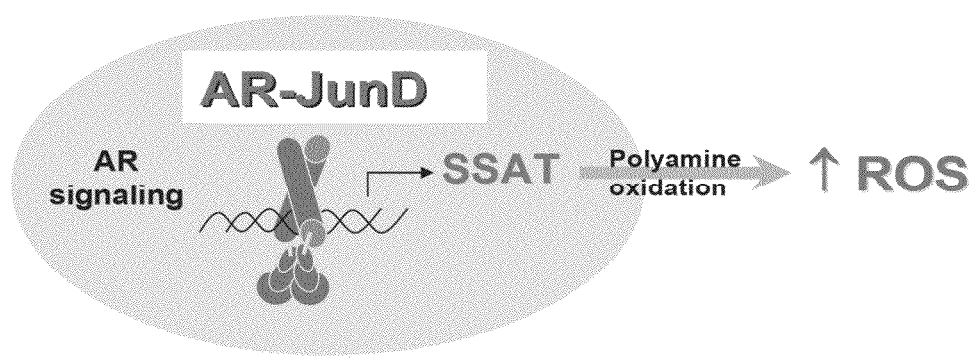
FIG. 7b shows a schematic representation of a major androgen-induced ROS production.

Described herein are JunD complexes with activated AR to mediate androgen-induced SSAT gene expression that results in ROS production due to spermidine and spermine oxidation as shown schematically in FIG. 7b. Also described herein are specific inhibitor(s) that block JunD-AR complex formation which in some embodiments, block androgen-induced ROS production and prevent prostate cancer occurrence and progression.

In some embodiments the structures of the inhibitor compounds described herein have a structural feature containing fused aromatic rings. In other embodiments, the fused aromatic ring moiety enables these compounds to bind to the JunD-AR interaction site to disrupt that interaction. Therefore, in other embodiments, molecular modeling studies of the JunD-AR interaction site are performed in silico and utilize the common structural feature of some of the inhibitors described herein to that, in other embodiments, specifically target JunD-AR interaction.

Data published from our and other laboratories have established that androgens induce ROS production in PCa cells. We have identified two factors: (A) transcription factor JunD is overexpressed in human PCa cells, when androgen induces oxidative stress and (B) androgen induces upregulation of SSAT, the first enzyme in a polyamine catabolic pathway that produces copious amounts of H$_2$O$_2$ in PCa cells containing very high amounts of polyamines.

We have used a *Gaussia* luciferase reconstitution assay in a high throughput screen to identify inhibitors of JunD-AR interaction. We have identified compounds that in some embodiments inhibit JunD-AR interaction. In one embodiment, some of these compounds effectively blocked androgen-induced ROS generation and showed a growth inhibitory effect.

Also presented herein are small molecule, small peptide, small peptidomimetics that block the interaction based on, in some embodiments, a common structural feature(s) of these inhibitors, such that they fit into the JunD-AR binding site(s). In other embodiments, peptides and/or peptidomimetics will more specifically target the JunD-AR interaction and inhibit androgen-induced ROS production specifically in PCa cells, avoiding side effects due to non-specific interaction often seen with small molecule inhibitors. Selected inhibitors are synthesized, optimized by testing in cultured human PCa cells and at least two of the most active inhibitors are further tested in PCa animal models.

Described herein are inhibitors of the AR-JunD interaction that in some embodiments inhibit androgen-induced reactive oxygen species (ROS) production in androgen dependent prostate cells, and thereby, prevent prostate cancer occurrence and progression.

Molecular Mechanism of AR Induced SSAT Activation:

Using Chromatin ImmunoPrecipitation (ChIP) assay, we have demonstrated that JunD associates with the SSAT promoter only in androgen-treated PCa cells and silencing JunD blocks AR-induced activation of SSAT gene transcription and ROS production in these cells.

Figure 8:
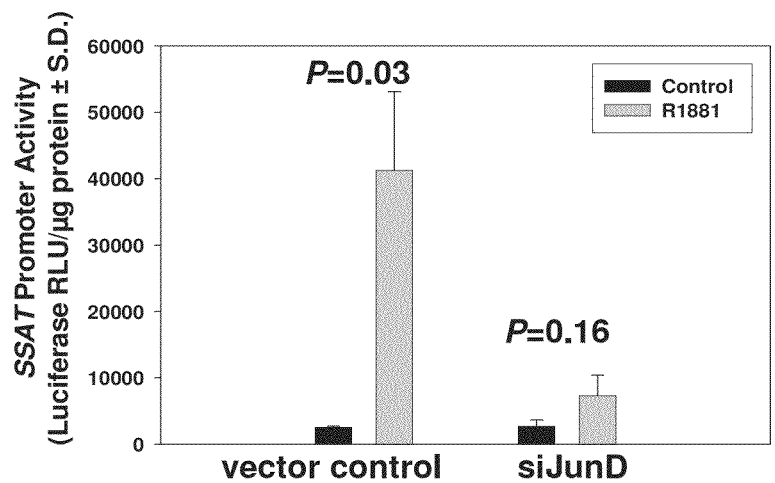
FIG. 8 shows luciferase reporter activity in SSAT-luc transfected control and JunD silenced (siJunD) LNCaP cells either vehicle treated (black bar) or treated with 1 nM R1881 (grey bar).

JunD is Necessary to Induce SSAT Gene Expression after Androgen Treatment:

In order to show that JunD complexes with AR to induce SSAT, we have constructed two LNCaP cell lines—one has been stably transfected with siJunD siRNA (siJunD), the other has been stably transfected with a control vector containing a scrambled siRNA sequence (vec. cont.). Both lines were transiently transfected with a SSAT promoter-luciferase reporter vector (SSAT-luc). The data were obtained as relative light units (RLU) produced by the luciferase enzyme per g protein that represents SSAT promoter activation after androgen analog R1881 treatment. The results are shown in FIG. 8. Nearly 10-fold decrease in R1881-induced SSAT promoter activation was observed in siJunD cells as compared to that in vec. cont. cells. These and other similar repeat data demonstrate that JunD is necessary for androgen-induced SSAT activation. Chromatin ImmunoPrecipitation assay (ChIP) assay confirms these data and also demonstrates that JunD is associated with SSAT promoter sequence only in androgen-treated cells.

Figure 9:
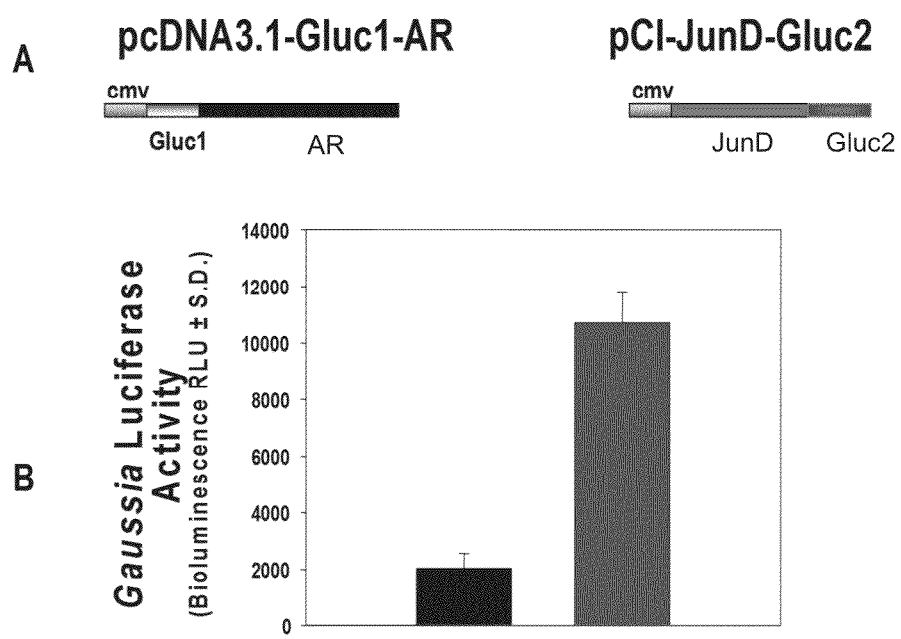
FIG. 9 shows (A) vector inserts with GL-AR and JunD-GL. (B) GL activity without (black bar) or with (red bar) R1881 treatment.

JunD-AR Complex Formation in Live Cells:

In order to confirm and quantitate the extent of JunD-AR complex formation in situ, the method of the *Gaussia* luciferase (GL) enzyme reconstitution assay was used. In this method, the GL gene sequence is divided into two parts—the N-terminal part is connected to the N-terminal of AR and the C-terminal part to the C-terminal of JunD in two separate expression vectors as shown in FIG. 9A. Cells co-transfected with both vectors would reconstitute GL activity only after JunD-AR complex formation in situ. The two vectors were co-transfected into Hep3B liver carcinoma cells with no AR background. Two hours after transfection, the cells are treated with the androgen analog R1881 for 48 hours in fresh medium and the cells are assayed for GL activity. The results are shown in FIG. 9B. Almost 10-fold enhancement in GL activity was observed in androgen-treated Hep3B cells as compared to untreated cells, demonstrating JunD-AR interaction in situ only in androgen-treated cells.

Figure 10:
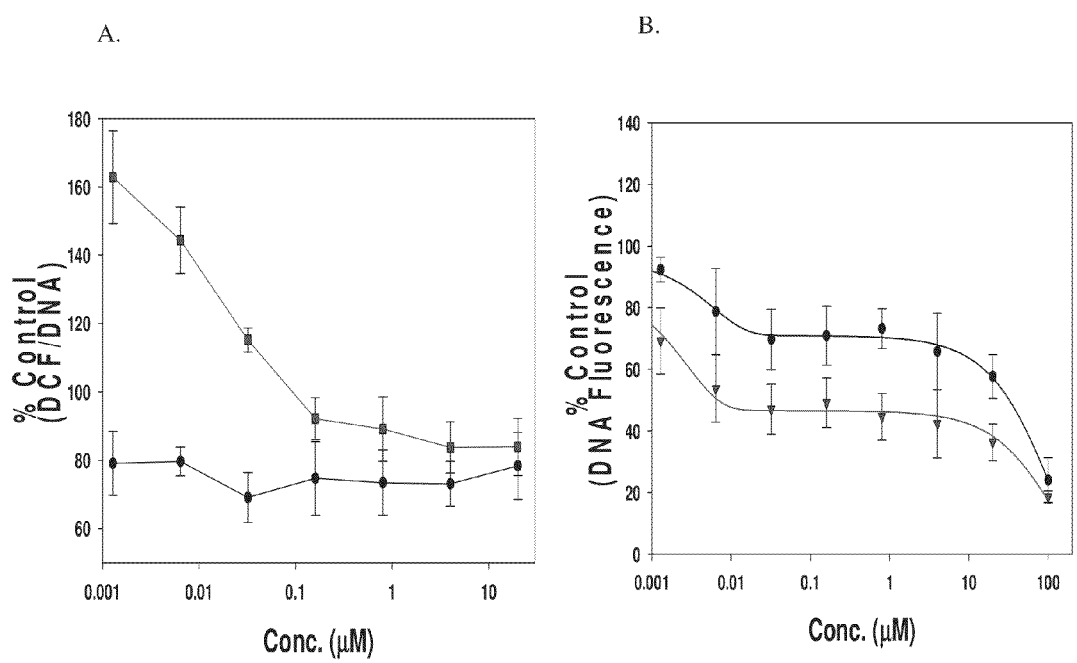
FIG. 10 shows (A) effect of 2,2'-(hydrazine-1,1-diyl)diacetic acid on ROS level of control (black) and R1881 (red) treated LNCaP cells. (B) effect of 2,2'-(hydrazine-1,1-diyl) diacetic acid on the growth of control (black) and R1881 (red) treated LNCaP cells.

This assay was employed for high-throughput-screening (HTS) of a NCI diversity set library containing drug-like molecules. In some embodiments, inhibitors of JunD-AR interaction from this library are described herein. In some embodiments, the data of the effect of at least one of the compounds on cell growth and androgen-induced ROS levels in LNCaP cells are shown in FIG. 10. The data show in some embodiments marked inhibition of androgen-induced ROS production at sub-micromolar concentration (FIG. 10A) and a strong growth inhibitory activity ($IC_{50}$<1 M) against cells growing either in the presence or in the absence of androgen (FIG. 100B).

Definitions

Before the disclosure is described in detail, it is understood that the scope of this disclosure is not limited to the particular methodology, protocols, cell lines, and reagents described, as these may vary. It is also to be understood that the terminology used herein is for the purpose of describing particular embodiments only and is not intended to limit the scope of the disclosure, which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

A cell can be in vitro. Alternatively, a cell can be in vivo and can be found in a subject. A "cell" can be a cell from any organism including, but not limited to, a bacterium or a mammalian cell.

As used throughout, by a "subject" is meant an individual. Thus, the "subject" can include domesticated animals, such as cats, dogs, etc., livestock (e.g., cattle, horses, pigs, sheep, goats, rabbits, etc.), laboratory animals (e.g., mouse, rabbit, rat, guinea pig, ferret, mink, etc.) and birds. In one aspect, the subject is a higher mammal such as a primate or a human.

In one aspect, the compounds described herein can be administered to a subject comprising a human or an animal including, but not limited to, a primate, murine, canine, feline, equine, bovine, porcine, caprine or ovine species and the like, that is in need of alleviation or amelioration from a recognized medical condition.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "moiety" defines a carbon containing residue, i.e. a moiety comprising at least one carbon atom, and includes but is not limited to the carbon-containing groups defined hereinabove. Organic moieties can contain various heteroatoms, or be bonded to another molecule through a heteroatom, including oxygen, nitrogen, sulfur, phosphorus, or the like. Examples of organic moieties, include but are not limited to alkyl or substituted alkyls, alkoxy or substituted alkoxy, mono or di-substituted amino, amide groups, etc. Organic moieties can preferably comprise 1 to 21 carbon atoms, 1 to 18 carbon atoms, 1 to 15, carbon atoms, 1 to 12 carbon atoms, 1 to 8 carbon atoms, or 1 to 4 carbon atoms.

Unless defined otherwise, all technical and scientific terms used herein have the same meanings as commonly understood by one of ordinary skill in the art. Although any methods and materials similar or equivalent to those described herein can be used in the practice or testing of the present disclosure, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the embodiments described herein.

The term "alkyl" denotes a moiety containing a saturated, straight or branched hydrocarbon residue having from 1 to 18 carbons, or preferably 4 to 14 carbons, 5 to 13 carbons, or 6 to 10 carbons. An alkyl is structurally similar to a non-cyclic alkane compound modified by the removal of one hydrogen from the non-cyclic alkane and the substitution, therefore, with a non-hydrogen group or moiety. Alkyl moieties can be branched or unbranched. Lower alkyl moieties have 1 to 4 carbon atoms. Examples of alkyl moieties include methyl, ethyl, n-propyl, iso-propyl, n-butyl, sec-butyl, t-butyl, amyl, t-amyl, n-pentyl and the like.

The term "substituted alkyl" denotes an alkyl moiety analogous to the above definition that is substituted with one or more organic or inorganic substituent moieties. In some embodiments, 1 or 2 organic or inorganic substituent moieties are employed. In some embodiments, each organic substituent moiety comprises between 1 and 4, or between 5 and 8 carbon atoms. Suitable organic and inorganic substituent moieties include, but are not limited to, hydroxyl, halogens, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, heteroaryl, substituted heteroaryl, aryl or substituted aryl. When more than one substituent group is present then they can be the same or different.

Abbreviations used herein include:

The term "alkoxy" as used herein denotes an alkyl moiety, defined above, attached directly to a oxygen to form an ether residue. Examples include methoxy, ethoxy, n-propoxy, iso-propoxy, n-butoxy, t-butoxy, iso-butoxy and the like.

The term "substituted alkoxy" denotes an alkoxy moiety of the above definition that is substituted with one or more groups, but preferably one or two substituent groups including hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they can be the same or different.

The term "mono-substituted amino" denotes an amino ($—NH_2$) group substituted with one group selected from alkyl, substituted alkyl or arylalkyl wherein the terms have the same definitions found throughout.

The term "di-substituted amino" denotes an amino substituted with two moieties that can be the same or different selected from aryl, substituted aryl, alkyl, substituted alkyl or arylalkyl, wherein the terms have the same definitions found throughout. Some examples include dimethylamino, methylethylamino, diethylamino and the like.

The term "haloalkyl" denotes a alkyl moiety, defined above, substituted with one or more halogens, preferably fluorine, such as a trifluoromethyl, pentafluoroethyl and the like.

The term "haloalkoxy" denotes a haloalkyl, as defined above, that is directly attached to an oxygen to form a halogenated ether residue, including trifluoromethoxy, pentafluoroethoxy and the like.

The term "acyl" denotes a moiety of the formula $—C(O)—R$ that comprises a carbonyl ($C=O$) group, wherein the R moiety is an organic moiety having a carbon atom bonded to the carbonyl group. Acyl moieties contain 1 to 8 or 1 to 4 carbon atoms. Examples of acyl moieties include but are not limited to formyl, acetyl, propionyl, butanoyl, iso-butanoyl, pentanoyl, hexanoyl, heptanoyl, benzoyl and like moieties.

The term "acyloxy" denotes a moiety containing 1 to 8 carbons of an acyl group defined above directly attached to an oxygen such as acetyloxy, propionyloxy, butanoyloxy, iso-butanoyloxy, benzoyloxy and the like.

The term "aryl" denotes an unsaturated and conjugated aromatic ring moiety containing 6 to 18 ring carbons, or preferably 6 to 12 ring carbons. Many aryl moieties have at least one six-membered aromatic "benzene" moiety therein. Examples of such aryl moieties include phenyl and naphthyl.

The term "substituted aryl" denotes an aryl ring moiety as defined above that is substituted with or fused to one or more organic or inorganic substituent moieties, which include but are not limited to a halogen, alkyl, substituted alkyl, haloalkyl, hydroxyl, cycloalkyl, substituted cycloalkyl, cycloalkenyl, substituted cycloalkenyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy, aryl, substituted aryl, heteroaryl, heterocyclic ring, substituted heterocyclic ring moiety, wherein the terms are defined herein. Substituted aryl moieties can have one, two, three, four, five, or more substituent moieties. The substituent moieties can be not be of unlimited size or molecular weight, and each organic moiety can comprise 15 or fewer, 10 or fewer, or 4 or fewer carbon atoms unless otherwise expressly contemplated by the claims.

The term "heteroaryl" denotes an aryl ring moiety as defined above, wherein at least one of the carbons of the aromatic ring has been replaced with a heteroatom, which include but are not limited to nitrogen, oxygen, and sulfur atoms. Heteroaryl moieties include 6 membered aromatic ring moieties, and can also comprise 5 or 7 membered aromatic rings, or bicyclic or polycyclic heteroaromatic rings as well. Examples of heteroaryl moieties include pyridyl, bipyridyl, furanyl, and thiofuranyl residues. It is to be understood that the heteroaryl moieties can optionally be substituted with one or more organic or inorganic substituent moieties bound to the carbon atoms of the heteroaromatic rings, as described hereinabove for substituted aryl moieties. Substituted heteroaryl moieties can have one, two, three, four, five, or more substituent organic or inorganic moieties, in a manner analogous to the substituted aryl moieties defined herein. The substituent moieties cannot be of unlimited size or molecular weight, and each organic substituent moiety can comprise 15 or fewer, 10 or fewer, or four or fewer carbon atoms unless otherwise expressly contemplated by the claims.

The term "halo," "halide," or "halogen" refers to a fluoro, chloro, bromo or iodo atom or ion.

The term "heterocycle" or "heterocyclic", as used in the specification and concluding claims, refers to a moiety having a closed ring structure comprising 3 to 10 ring atoms, in which at least one of the atoms in the ring is an element other than carbon, such as, for example, nitrogen, sulfur, oxygen, silicon, phosphorus, or the like. Heterocyclic compounds having rings with 5, 6, or 7 members are common, and the ring can be saturated, or partially or completely unsaturated. The heterocyclic compound can be monocyclic, bicyclic, or polycyclic. Examples of heterocyclic compounds include but are not limited to pyridine, piperidine, thiophene, furan, tetrahydrofuran, and the like. The term "substituted heterocyclic" refers to a heterocyclic moiety as defined above having one or more organic or inorganic substituent moieties bonded to one of the ring atoms.

The term "carboxy", as used in the specification and concluding claims, refers to the —C(O)OH moiety that is characteristic of carboxylic acids. The hydrogen of the carboxy moieties is often acidic and (depending on the pH) often partially or completely dissociates, to form an acid H+ ion and a carboxylate anion (—$CO_2$—), wherein the carboxylate anion is also sometimes referred to as a "carboxy" moiety.

It is understood that when a chiral atom is present in a compound disclosed herein, both separated enantiomers, racemic mixtures and mixtures of enantiomeric excess are within the scope of the present disclosure. As defined herein, racemic mixture is an equal ratio of each of the enantiomers, whereas an enantiomeric excess is when the percent of one enantiomer is greater than the other enantiomer, all percentages are within the scope of the present disclosure. Furthermore, when more than one chiral atom is present in a compound then the enantiomers, racemic mixtures, mixtures of enantiomeric excess and diastereomeric mixtures are within the scope of the present disclosure.

Methods of Treatment

In view of their ability to inhibit or disrupt the JunD-AR interaction, the compounds described herein can be used to prevent, alleviate or otherwise treat diseases of uncontrolled proliferation in mammals, including humans, such as cancer or precancerous diseases. The compounds described herein can be used for the preparation of medicaments for treating diseases of uncontrolled inflammation, proliferation, hyperplasis, cancers including and not limited to and prostate disease and cancer.

Therefore, in some embodiments, the present disclosure relates to methods of treatment for a disease of uncontrolled cellular inflammation, proliferation, wherein the method comprises administering to a mammal diagnosed as having a disease of uncontrolled cellular inflammation and/or proliferation a compound of the present disclosure or a pharmaceutical composition thereof comprising one or more of the compounds of the present disclosure, in an amount that is effective to treat the disease of uncontrolled cellular inflammation and/or proliferation.

The disease of uncontrolled cellular inflammation and/or proliferation treated can be a carcinoma, lymphoma, leukemia, or sarcoma. The types of cancer treated by methods of the present disclosure include but are not limited to Hodgkin's Disease, myeloid leukemia, polycystic kidney disease, bladder cancer, brain cancer, head and neck cancer, kidney cancer, lung cancer, myeloma, neuroblastoma/glioblastoma, ovarian cancer, pancreatic cancer, prostate cancer, skin cancer, liver cancer, melanoma, colon cancer, cervical carcinoma, breast cancer, epithelial cancer, and leukemia. The compositions can also be used as regulators in diseases of uncontrolled inflammation and/or proliferation and/or precancerous conditions such as cervical and anal dysplasias, other dysplasias, severe dysplasias, hyperplasias, atypical hyperplasias, prostatic intraepithelial neoplasms, and neoplasias.

In some embodiments, the embodiments described herein relate to methods for treating or inhibiting the occurrence, recurrence, progression or metastasis, of a cancer or a neoplasia precursor thereof, consisting of administering to a mammal diagnosed as having or being susceptible to a cancer or precursor neoplasia thereof, in an amount effective to treat the cancer or inhibit the occurrence, recurrence, progression, or metastasis of the cancer or precursor neoplasia thereof, one or more pharmaceutically acceptable salts.

The pharmaceutically acceptable salts of the present disclosure have been found to be particularly effective in treating certain cancers, including, but not limited to prostate cancer, colorectal cancer, gastric cancer, renal cancer, skin cancer, head and neck cancer, brain cancer, pancreatic cancer, lung cancer, ovarian cancer, uterine cancer, liver cancer, and breast cancer.

In some embodiments, the present disclosure relates to method for treating, or inhibiting the occurrence, recurrence, progression or metastasis of prostate cancer, consisting of administering to a mammal diagnosed as having prostate cancer or precursor neoplasia thereof, in an amount effective to treat the cancer or inhibit the occurrence, recurrence, progression, or metastasis of the prostate cancer or precursor neoplasia thereof, one or more pharmaceutically acceptable salts of the present disclosure comprising an inhibitor of the JunD-AR interaction.

Pharmaceutical Compositions

Although the compounds described herein can be administered as pure chemicals either singularly or plurally, it is preferable to present the active ingredient as a nutraceutical or pharmaceutical composition. Thus, another embodiment of the present disclosure is the use of a pharmaceutical composition comprising one or more compounds and/or a pharmaceutically acceptable salt thereof, together with one or more pharmaceutically acceptable carriers thereof and, optionally, other therapeutic and/or prophylactic ingredients. The carrier(s) should be "acceptable" in the sense of being compatible with the other ingredients of the composition and not overly deleterious to the recipient thereof. The pharmaceutical composition is administered to a mammal diagnosed as in need of treatment for a disease of uncontrolled cellular inflammation and/or proliferation, in an amount effective to treat the disease of uncontrolled cellular inflammation and/or proliferation, such as the various cancers and precancerous conditions described herein.

As used herein, "pharmaceutical composition" means therapeutically effective amounts of a pharmaceutically effective compound together with suitable combination of one or more pharmaceutically-acceptable carriers, many of which are known in the art, including diluents, preservatives, solubilizers, emulsifiers, and adjuvants, collectively".

As used herein, the terms "effective amount" and "therapeutically effective amount" refer to the quantity of active therapeutic agent sufficient to yield a desired therapeutic or preventative response, without undue adverse side effects, such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of an androgen-mediated or androgen-independent disorder (e.g., prostate cancer); and (b) the reversal or stabilization of an androgen-mediated or androgen-independent disorder (e.g., prostate cancer). The optimum effective amounts can be readily determined by one of ordinary skill in the art using routine experimentation.

Pharmaceutical compositions can be liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thiomersal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, gels, hydrogels, etc., or onto liposomes, microemulsions, micelles, nanoparticles, etc.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, anti-oxidants, collating agents, inert gases and the like.

Controlled or sustained release compositions administrable according to the present disclosure include formulation in lipophilic depots (e.g. fatty acids, waxes, oils). Also comprehended by the present disclosure are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the present disclosure incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding modified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the present disclosure, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14: 201 (1987); Buchwald et al., Surgery 88: 507 (1980); Saudek et al., N. Engl. J. Med. 321: 574 (1989). In another embodiment, polymeric materials can be used. In yet another embodiment, a controlled release system can be placed in proximity to the therapeutic target, i.e., the prostate, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249: 1527-1533 (1990)).

The pharmaceutical preparation can comprise the anti-androgen compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories.

Pharmaceutically acceptable carriers include gums, starches, sugars, cellulosic materials, and mixtures thereof. The pharmaceutical preparation containing the compound can be administered to a patient by, for example, subcutaneous implantation of a pellet. In a further embodiment, a pellet provides for controlled release of compound over a period of time. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

Though it is not possible to specify a single predetermined pharmaceutically effective amount of the compounds of the present disclosure, and/or their pharmaceutical compositions, for each and every disease condition to be treated, determining such pharmaceutically effective amounts are within the skill of, and ultimately at the discretion of an attendant physician or clinician of ordinary skill. In some embodiments, the active compounds of the present disclosure are administered to achieve peak plasma concentrations of the active compound of from typically about 0.01 to about 100 µM, about 1 to 50 µM, about 0.01 to about 10 M, about 0.02 to about 1 M, about 0.03 to about 0.1 M, about 0.05 to about 0.5 M, about 0.06 to about 0.1 M, about 2 to about 30 µM. This can be achieved, for example, by the intravenous injection of a 0.05% to 5% solution of the active ingredient, optionally in saline, or orally administered as a bolus containing about 0.5-1000 mg of the active ingredient. Desirable blood levels can be maintained by continuous infusion to provide about 0.01-5.0 mg/kg/hr or by intermittent infusions containing about 0.4-15 mg/kg of the active compounds of the present disclosure.

Pharmaceutical compositions include those suitable for oral, enteral, parental (including intramuscular, subcutaneous and intravenous), topical, nasal, vaginal, ophthalmic sublingual, nasal or by inhalation administration. The compositions can, where appropriate, be conveniently presented in discrete unit dosage forms and can be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

The compounds of the present disclosure can have oral bioavailability as exhibited by blood levels after oral dosing, either alone or in the presence of an excipient. Oral bioavailability allows oral dosing for use in chronic diseases, with the advantage of self-administration and decreased cost over other means of administration. Pharmaceutical compositions suitable for oral administration can be presented as discrete unit dosage forms such as hard or soft gelatin capsules, cachets or tablets each containing a predetermined amount of the active ingredient; as a powder or as granules; as a solution, a suspension or as an emulsion. The active ingredient can also be presented as a bolus, electuary or paste. Tablets and capsules for oral administration can contain conventional excipients such as binding agents, fillers, lubricants, disintegrants, or wetting agents. The tablets can be coated according to methods well known in the art., e.g., with enteric coatings.

Oral liquid preparations can be in the form of, for example, aqueous or oily suspensions, solutions, emulsions, syrups or elixirs, or can be presented as a dry product for constitution with water or other suitable vehicle before use. Such liquid preparations can contain conventional additives such as suspending agents, emulsifying agents, non-aqueous vehicles (which can include edible oils), or one or more preservative.

The pharmaceutical preparations administrable by the present disclosure can be prepared by known dissolving, mixing, granulating, or tablet-forming processes. For oral administration, the compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules or supercritically formulated nanoparticles.

The compounds can also be formulated for parenteral administration (e.g., by injection, for example, bolus injection or continuous infusion) and can be presented in unit dose form in ampules, pre-filled syringes, small bolus infusion containers or in multi-does containers with an added preservative. The compositions can take such forms as suspensions, solutions, or emulsions in oily or aqueous vehicles, and can contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g., sterile, pyrogen-free water, before use.

For parenteral administration (subcutaneous, intravenous, intra-arterial, or intramuscular injection), the compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

The compounds of the present disclosure comprise cationic anti-oxidants in the form pharmaceutically acceptable salt with pharmaceutically acceptable anions. Pharmaceutically acceptable salts include pharmaceutically acceptable halides such as fluoride, chloride, bromide, or iodide, tribasic phosphate, dibasic hydrogen phosphate, monobasic dihydrogen phosphate, or the anionic forms of pharmaceutically acceptable organic carboxylic acids as acetates, triflates, oxalates, tartrates, mandelates, succinates, citrates, and the like. Such pharmaceutically acceptable salts can be readily synthesizes from other salts used for the initial synthesis of the compounds by ion exchange reactions and technologies well known to those of ordinary skill in the art.

Salts formed from any free carboxyl groups on the cationic antioxidant moieties can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the anti-oxidant, anti-cancer or chemo-therapeutic or chemo-preventative compound may be pharmaceutically acceptable salts. Other salts may, however, be useful in the commercial or laboratory preparation of the compounds according to the present disclosure or of their pharmaceutically acceptable salts. Suitable pharmaceutically acceptable salts of the compounds include acid addition salts which may, for example, be formed by mixing a solution of the compound according to the present disclosure with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In addition, the salts described herein may be provided in the form of nutraceutical compositions where the anti-oxidant, and other desirable properties of the salts prevents the onset of or reduces or stabilizes various conditions or disorders, e.g., including inhibiting the occurrence various forms of cancer, including prostate cancer, although the bottle label may not use such terms. The term "nutraceutical," or "nutraceutical composition," for the purposes of this specification, refers to a food item, or a part of a food item, that offers medical health benefits, including prevention and/or treatment of disease. A nutraceutical composition according to the present disclosure may contain only a cationic antioxidant compound according to the present disclosure as an active ingredient or, alternatively, may further comprise, in admixture with the aforesaid cationic antioxidant compound, dietary supplements including vitamins, co-enzymes, minerals, herbs, amino acids and the like which supplement the diet by increasing the total intake of that substance.

Therefore, the present disclosure provides methods of providing nutraceutical benefits to a patient comprising the step of administering to the patient a nutraceutical composition containing a compound having Formula I or a pharmaceutically acceptable salt thereof. Such compositions generally include a "nutraceutically-acceptable carrier" which, as referred to herein, is any carrier suitable for oral delivery including, but not limited to, the aforementioned pharmaceutically-acceptable carriers. In certain embodiments, nutraceutical compositions according to the present disclosure comprise dietary supplements which, defined on a functional basis, include immune boosting agents, anti-inflammatory agents, anti-oxidant agents, or mixtures thereof.

Although some of the supplements listed above have been described as to their pharmacological effects, other supplements may also be utilized in the present disclosure and their effects are well documented in the scientific literature.

In general, one of skill in the art understands how to extrapolate in vivo data obtained in a model organism, such as athymic nude mice inoculated with human tumor cell lines, to another mammal, such as a human. These extrapolations are not simply based on the weights of the two organisms, but rather incorporate differences in rates of metabolism, differences in pharmacological delivery, and administrative routes. Based on these types of considerations, a suitable dose will in alternative embodiments, typically be in the range of from about 0.5 to about 10 mg/kg/day, or from about 1 to about 20 mg/kg of body weight per day, or from about 5 to about 50 mg/kg/day.

The desired dose can conveniently be presented in a single dose or as divided doses administered at appropriate intervals, for example, as two, three, four or more sub-doses per day. The sub-dose, as necessary by one skilled in the art, can itself be further divided, e.g., into a number of discrete loosely spaced administrations.

One skilled in the art will recognize that dosage and dosage forms outside these typical ranges can be tested and, where appropriate, be used in the methods presented herein.

Combinations

According to another aspect of the present disclosure, pharmaceutical compositions of matter useful for the treatment of cancer are provided that contain, in addition to the aforementioned compounds, an additional therapeutic agent. Such agents can be chemotherapeutic agents, ablation or other therapeutic hormones, anti-neoplastic agents, monoclonal antibodies useful against cancers and angiogenesis and other inhibitors. The following discussion highlights some agents in this respect, which are illustrative, not limitative. A wide variety of other effective agents also can be used.

Among hormones which can be used in combination with the present inventive compounds, diethylstilbestrol (DES), leuprolide, flutamide, hydroxyflutamide, bicalutamide, cyproterone acetate, ketoconazole, abiraterone, and amino glutethimide.

Among antineoplastic and anticancer agents that can be used in combination with the inventive compounds, Taxotere (Docetaxol), 5-fluorouracil, vinblastine sulfate, estramustine phosphate, suramin and strontium-89. Other chemotherapeutics useful in combination and within the scope of the present disclosure are buserelin, chlorotranisene, chromic phosphate, cisplatin, satraplatin, cyclophosphamide, dexamethasone, doxorubicin, estradiol, estradiol valerate, estrogens conjugated and esterified, estrone, ethinyl estradiol, floxuridine, goserelin, hydroxyurea, melphalan, methotrexate, mitomycin and prednisone.

EXAMPLES

The examples are provided for illustrative purposes only and not to limit the scope of the claims provided herein. The starting materials and reagents used for the synthesis of the compounds described herein may be synthesized or can be obtained from commercial sources, such as, but not limited to, Sigma-Aldrich, Acros Organics, Fluka, and Fischer Scientific.

Example 1

Synthesis of the Compounds Disclosed Herein

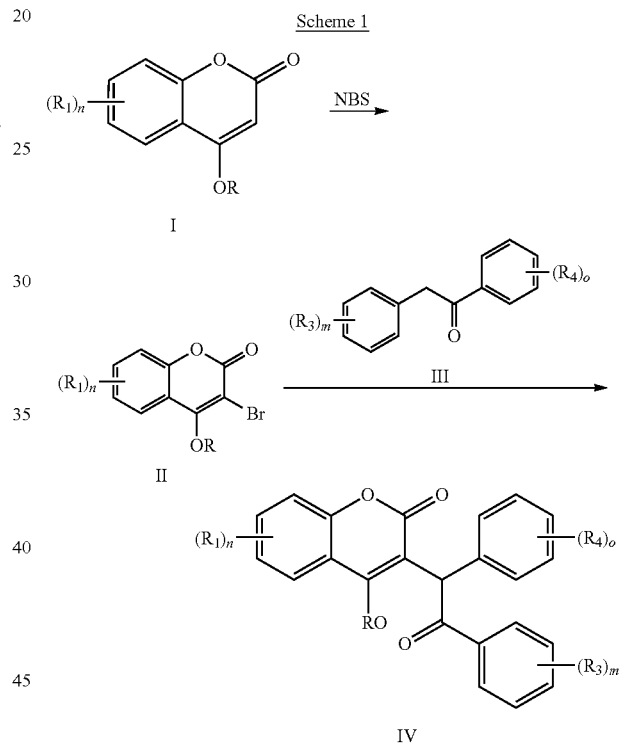

Compounds of Formula (I) are synthesized according to the method of Scheme 1. Briefly, bromination of I using NBS provides compound II. Reaction of III with compound II provides the desired compound IV. R, $R_1$, $R_3$, and $R_4$ are as described herein.

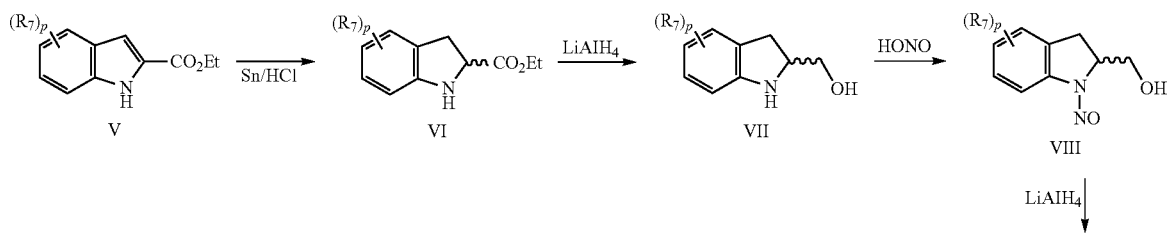

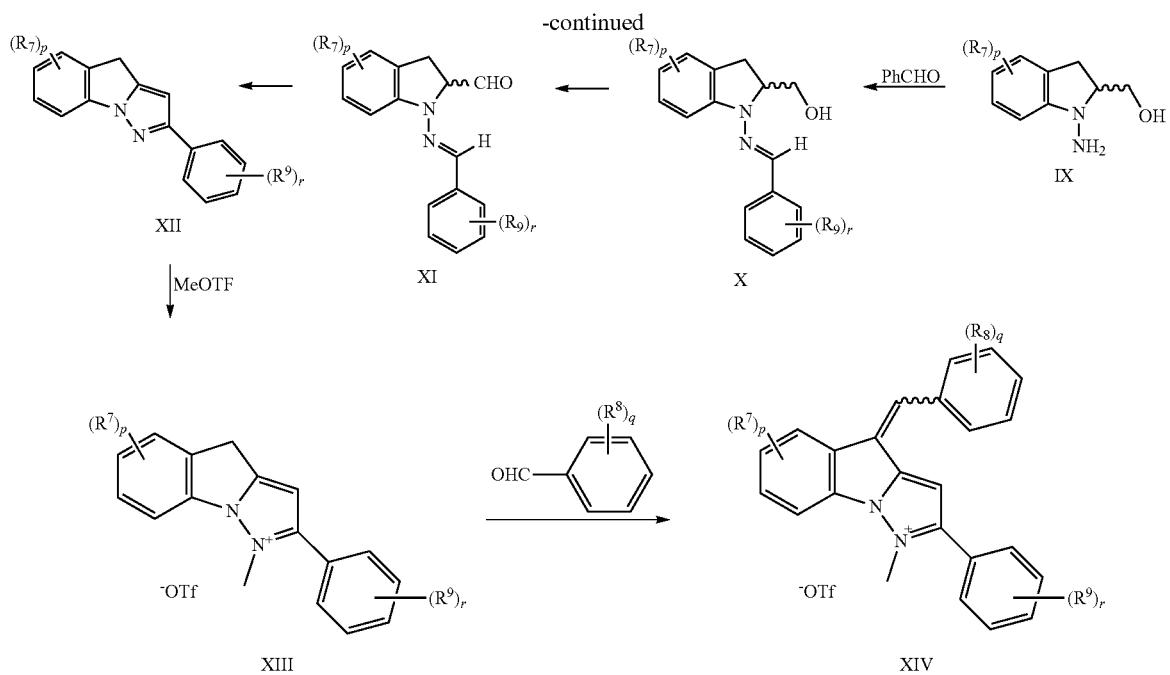

Compounds of Formula (II) are synthesized according to the method of Scheme 2. Briefly, reduction of compound V provides compound VI which undergoes further reduction to provide the alcohol VII. Reaction of VII with HONO provides the nitrosoamine VIII which is reduced to the amine compound IX. Reaction of the amine IX with benzaldehyde affords X. Oxidation of X provides the aldehyde, XI. Ring cyclization results in compound XII which is then reacted with methyltriflate to provide XIII. Coupling of the optionally substituted benzaldehyde provides the desired compound XIV. $R_7$, $R_8$, and $R_9$ are as described herein.

Synthesis of Other JunD-AR inhibitors

Synthesis of 2,2'-(hydrazine-1,1-diyl)diacetic acid: Monochloroacetic acid (2 eq.) in water was neutralized with potassium carbonate (1 eq.) followed by the addition of hydrazine hydrate (1 eq.). Potassium carbonate (1 eq.) was added to the solution gradually, whereupon, with a steady evolution of $CO_2$, the temperature rose to 70° C. The solution was then heated until the gas evolution stopped. At the end of the reaction, the 2,2'-(hydrazine-1,1-diyl)diacetic acid was precipitated by making the solution acidic with concentrated HCl. The product (mp 171° C.) was crystallized from water, and was confirmed by NMR spectroscopy and elemental analysis.

Synthesis of dimethyl 2,2'-(hydrazine-1,1-diyl)diacetate: 2,2'-(hydrazine-1,1-diyl)diacetic acid was suspended in MeOH and HCl gas was bubbled while cooling in an ice bath. As the reaction progressed and dimethyl 2,2'-(hydrazine-1,1-diyl)diacetate was formed, the suspension became clearer. The content was stirred overnight and solvent was evaporated to afford dimethyl 2,2'-(hydrazine-1,1-diyl)diacetate, (mp 166° C.). The structure was confirmed by NMR spectroscopy and elemental analysis.

Synthesis of 2,2'-(1,3-dioxoisoindolin-2-ylazanediyl)diacetic acid: Hydrazine monohydrate was reacted with phthalic acid to get a mono substituted pthalimide of hydrazine, which was bis-alkylated with monochloroacetic acid to afford crude 2,2'-(1,3-dioxoisoindolin-2-ylazanediyl)diacetic acid. The product was purified by column chromatography using silicagel and the structure was confirmed by Mass spectroscopy and elemental analysis.

Example 2

Biological Activity

The salts described above have been found to be potent compounds in a number of in vitro biological assays that correlate to or are representative of human diseases, especially diseases of uncontrolled cellular proliferation, including benign hyperplasia and various cancers.

The biological activity of the compounds described herein can be measured, screened, and/or optimized by testing the salts for their relative ability to kill or inhibit the growth of various human tumor cell lines and primary tumor cell cultures.

Figure 11:
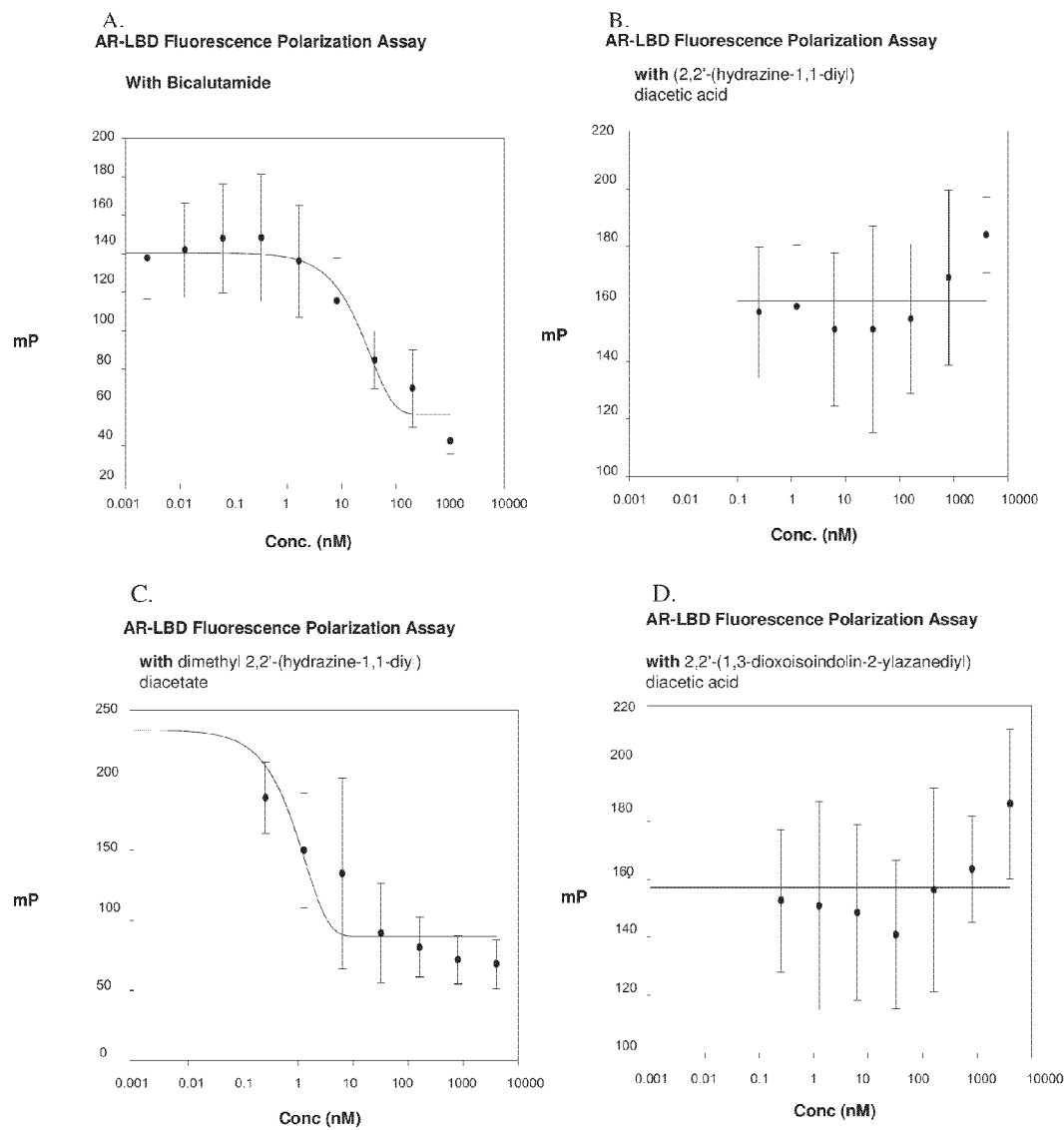
FIG. 11 shows the effect of bicalutamide and compounds disclosed herein on the fluorescence polarization of fluorescence tagged androgen-AR-LBD complex.

The anti-androgenic properties of the three compounds (2,2'-(hydrazine-1,1-diyl)diacetic acid, dimethyl 2,2'-(hydrazine-1,1-diyl)diacetate, 2,2'-(1,3-dioxoisoindolin-2-ylazanediyl)diacetic acid) were tested by a fluorescence polarization assay for Androgen Receptor Ligand Binding Domain (AR-LBD) binding studies standardized in our laboratories. Binding of bicalutamide with AR-LBD was used as a positive control. The results of the fluorescence polarization studies are shown in FIG. 11. While 2,2'-(hydrazine-1,1-diyl)diacetic acid and 2,2'-(1,3-dioxoisoindolin-2-ylazanediyl)diacetic acid showed no AR-LBD binding property, dimethyl 2,2'-(hydrazine-1,1-diyl)diacetate showed an interaction with the AR-LBD that is comparable with that of bicalutamide. Thus, we have derived at least three new drugs from our single "hit" in our screening assay that are expected to inhibit the AR-JunD interaction and thus, block androgen-induced oxidative stress in CaP cells. In addition, one of these compounds may be a potent anti-androgen.

Figure 12:
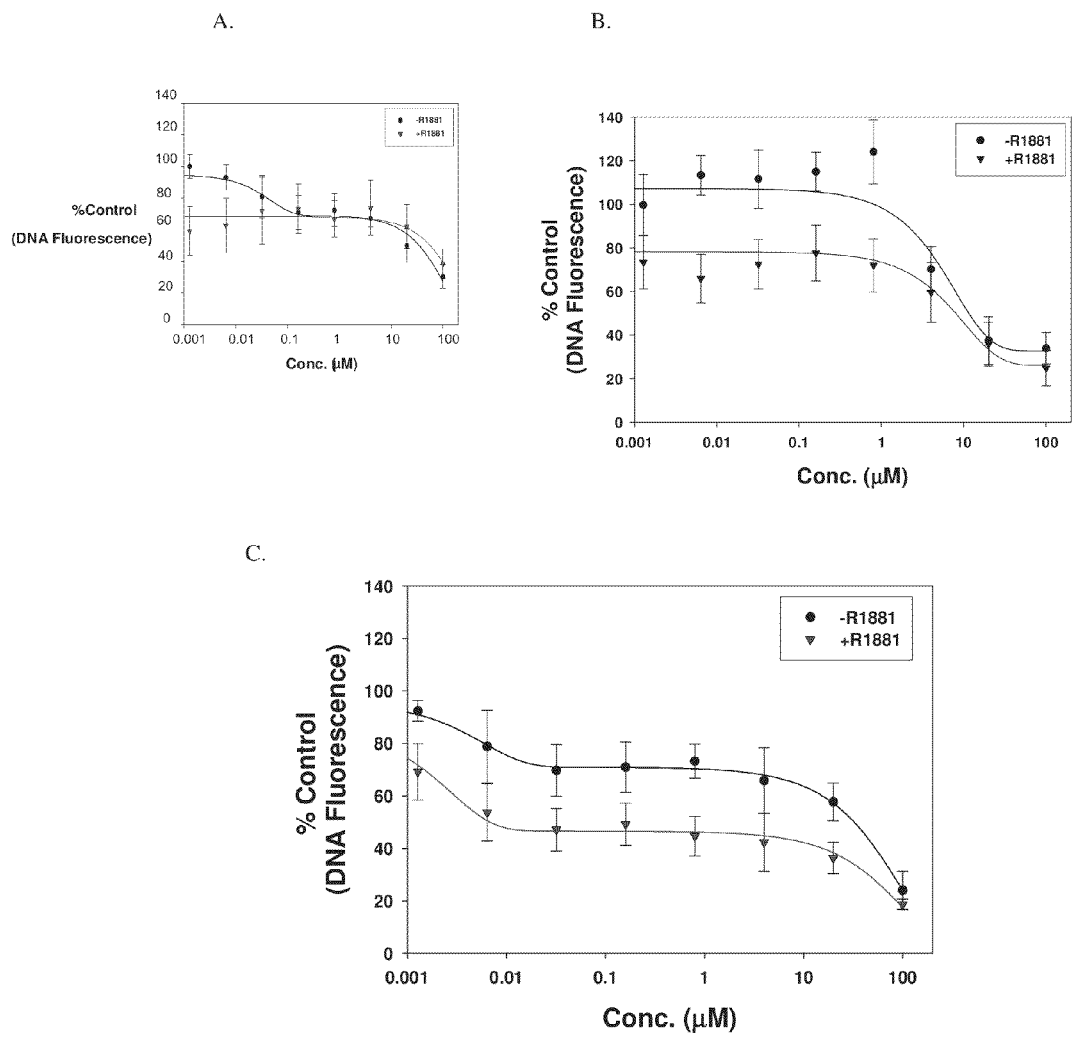
FIG. 12 shows Effect of (A) 2,2'-(hydrazine-1,1-diyl)diacetic acid, (B) dimethyl 2,2'-(hydrazine-1,1-diyl)diacetate and (C) 2,2'-(1,3-dioxoisoindolin-2-ylazanediyl)diacetic acid on the ROS levels of LNCaP cells in the absence (_ black) or presence ( . . . . . . . red) of 1 nM R1881.
Figure 15:
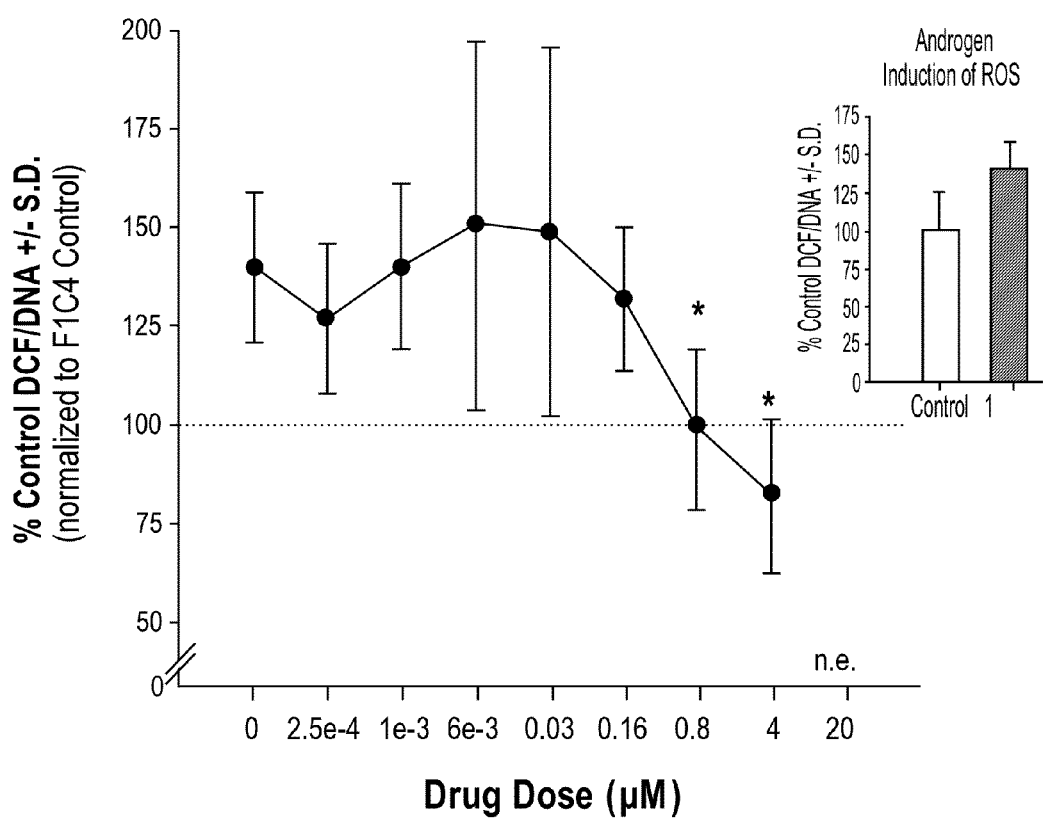
FIG. 15 shows that compound 71 blocks androgen induction of ROS in androgen-dependent LNCaP cells. Compound 71 was identified as the most effective compound for blocking androgen induction of ROS and inhibiting both androgen-dependent and androgen independent PCa cell growth.
Figure 16:
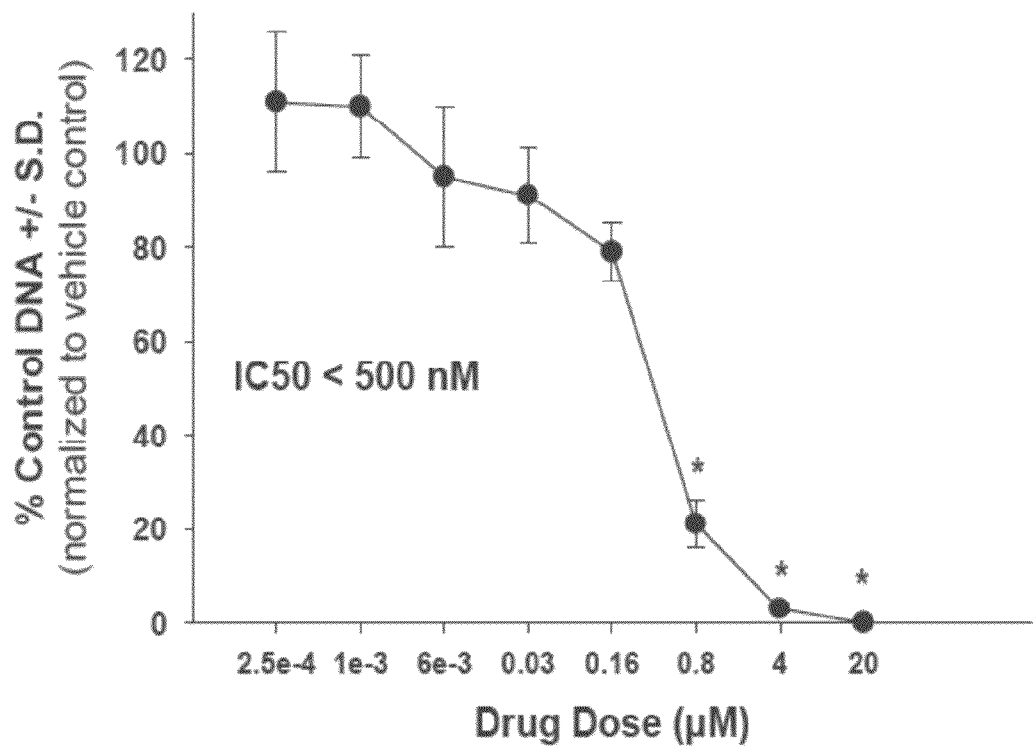
FIG. 16 shows inhibition by compound 71 of androgen-dependent LNCaP cell growth.
Figure 17:
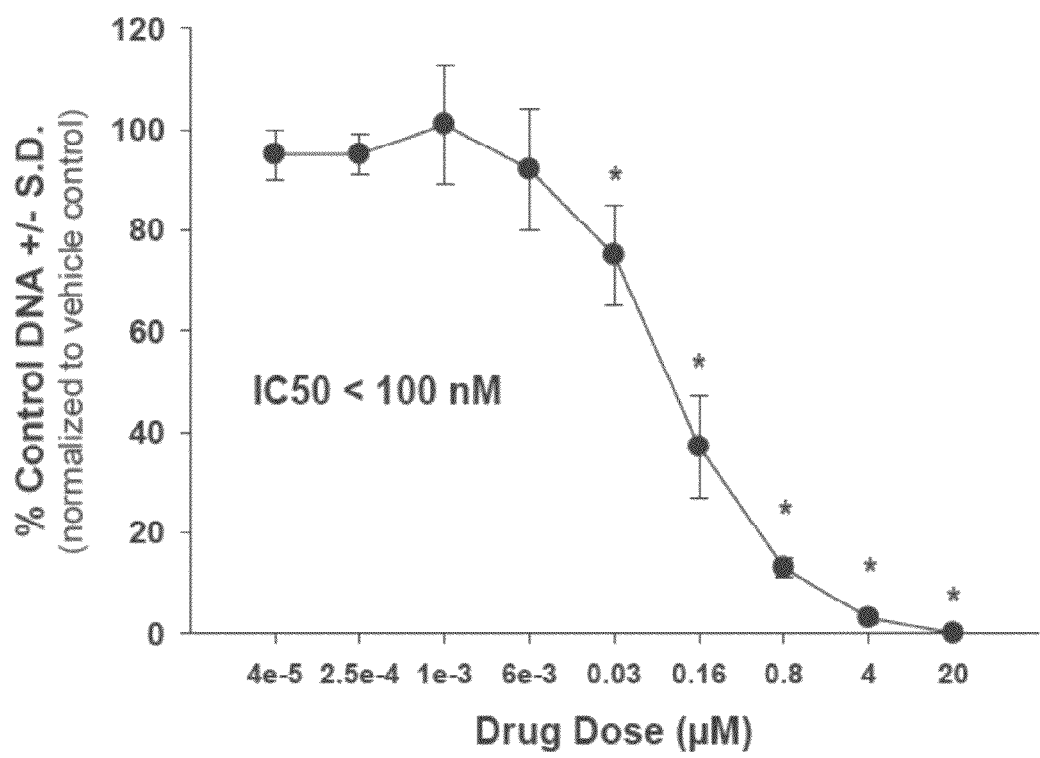
FIG. 17 shows inhibition by compound 71 of androgen-independent LNCaP $C_{4-2}B$ cell growth.
Figure 19:
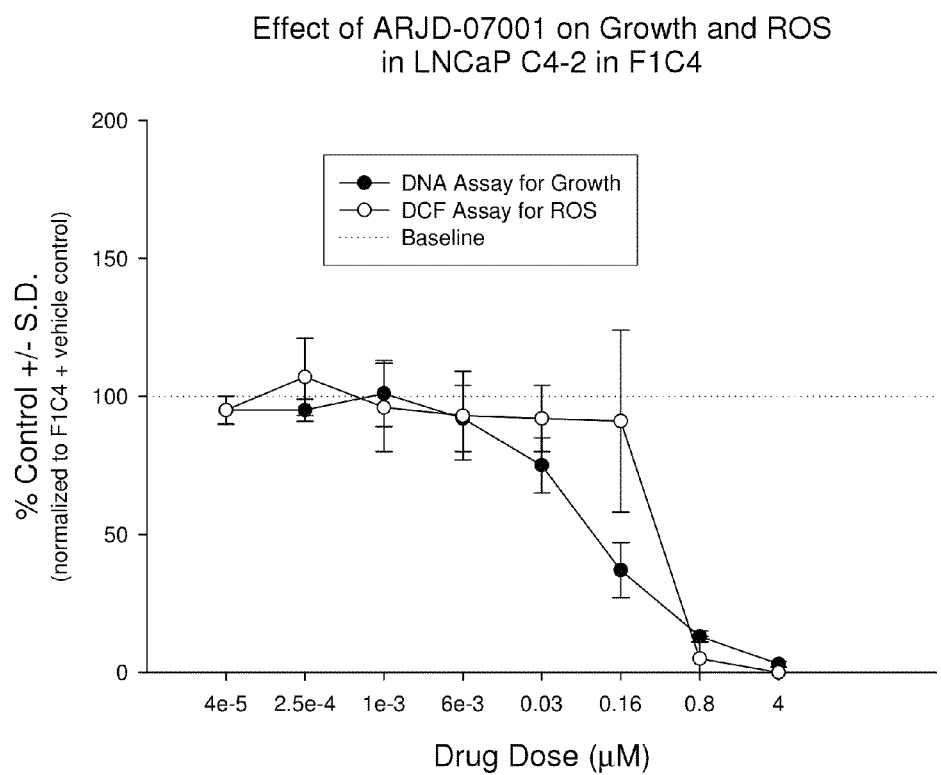
FIG. 19 shows the effect of 71 on ROS (open circle) and Growth (filled circle) treated androgen-independent LNCaP $C_{4-2}$ cells growing in low androgen (F1/C4) media.

Described herein are tests for the effect of these three compounds on the androgen-induced ROS production in androgen-dependent LNCaP cells using the DCF dye oxidation assay (see the complete proposal). The results are shown in FIG. 12. All data were normalized to the DCF dye fluorescence of control untreated LNCaP cells and expressed as percent of control. The data clearly demonstrate that both 2,2'-(hydrazine-1,1-diyl)diacetic acid and 2,2'-(1,3-dioxoisoindolin-2-ylazanediyl)diacetic acid) can successfully block androgen-induced ROS production in LNCaP cells at a concentration <1 µM. In addition, 2,2'-(hydrazine-1,1-diyl)diacetic acid also has a weak activity in reducing ROS levels in LNCaP cells that are not treated with R1881. On the other hand, dimethyl 2,2'-(hydrazine-1,1-diyl)diacetate has no effect on the ROS levels in LNCaP cells under any condition. These data demonstrate that a compound (2,2'-(hydrazine-1,1-diyl)diacetic acid) identified by the high throughput screening (HTS) assay can not only actively block androgen-induced oxidative stress in LNCaP cells, but in some embodiments also reduces ROS in LNCaP cells in the absence of R1881 possibly by disrupting any minor AR-JunD interaction in cells in the absence of androgen. The inactivity of dimethyl 2,2'-(hydrazine-1,1-diyl)diacetate also indicates that the COOH groups of this class of compounds are important in blocking AR-JunD interaction(s).

The growth inhibitory activities of the all three compounds against LNCaP cells growing both in the presence and absence of R1881 are shown in FIG. 12. While all three compounds showed growth inhibitory activities, 2,2'-(hydrazine-1,1-diyl)diacetic acid and 2,2'-(1,3-dioxoisoindolin-2-ylazanediyl)diacetic acid) exhibited growth inhibition at a sub-micromolar concentration, while dimethyl 2,2'-(hydrazine-1,1-diyl)diacetate inhibited cell growth only between 1-10 M range, which is comparable to that of bicalutamide and possibly due to its anti-androgenic properties. None of the compounds has any effect on the growth and ROS production in AR-negative PC-3 cells. The active compounds 2,2'-(hydrazine-1,1-diyl)diacetic acid and 2,2'-(1,3-dioxoisoindolin-2-ylazanediyl)diacetic acid) also have no anti-androgenic properties. These observations suggest that these compounds are active in the androgen signaling pathway related to ROS generation downstream to androgen-AR interaction.

Materials and Methods

Antibodies:

Primary antibodies: monoclonal antibody against the AR [AR (441)]; sc-7305; Santa Cruz Biotechnology, Santa Cruz, Calif.); polyclonal antibody against JunD (sc-74X, Santa Cruz); polyclonal antibody against *Gaussia* luciferase (Nanolight Technology, Pinetop, Ariz.); monoclonal antibody against β-actin (A5441; Sigma, St. Louis, Mo.). Secondary antibodies for immune-histochemistry: Alexa Fluorescent 594 goat anti-rabbit IgG (Invitrogen, Carlsbad, Calif.); Alexa Fluorescent 488 donkey anti-mouse IgG (Invitrogen).

Cell Culture:

Androgen sensitive LNCaP human prostate carcinoma cells were obtained from ATCC and maintained in DMEM supplemented with 10% FBS (F10 medium) as described previously (17). Hep3B human hepatoma cells were maintained in RPMI supplemented with 10% FBS and antibiotics. Cell lines are tested annually for mycoplasma.

Culture conditions for LNCaP androgen response studies included use of cells passage 40-90, hormone depleted media containing 4% charcoal-stripped FBS plus 1% non-stripped FBS (F1C4), and synthetic androgen R1881 (methyltrienolone; NEN, Boston, Mass.) at 1 nM for maximal induction of JunD and ROS as described before (17,19,20). For AR-JunD interaction studies in AR-transfected Hep3B cells, R1881 was used at 2 nM in F1C4 medium to maximally induce the AR.

Vector Construction:

cDNA coding for the human androgen receptor (AR) was obtained from Open Biosystems (Huntsville, Ala.). The whole human junD gene (20) was sub-cloned in a pCI-based vector (Promega, Madison, Wis.). Two sections of the humanized *Gaussia* luciferase gene, N-terminus hGluc1 and C-terminus hGluc2, in two separate vectors (30) were kind gifts from Prof. Stephen Michnick (University of Montreal, Canada). hGluc1 was cloned in frame with the N-terminal end of the AR in a pcDNA3.1-based vector (Invitrogen) to create the vector Gluc1-AR.

The pCI-junD vector was used to fuse hGluc2 in frame at the end of the junD gene after removing the junD stop codon to construct the vector JunD-Gluc2. The authenticity of each construct was verified by using Big Dye terminator and sequencing. The in-frame fusion of each construct was also verified by transfecting each into AR-negative Hep3B cells and analyzing cell lysate by western blot with AR antibody for Gluc1-AR or antibody for *Gaussia* luciferase at the C-terminal end of the fusion protein for JunD-Gluc2. β-actin was used to control for protein loading in all Western blot analyses.

Transfection of Constructs into Hep3B Cells:

$5 \times 10^5$ Hep3B cells were seeded, then one day later co-transfected with 3 g each of Gluc1-AR and JunD-Gluc2 constructs, or transfected with Gluc1-AR or JunD-Gluc2 alone as negative controls using Lipofectamine 2000 reagent (Invitrogen), following the manufacturer-supplied protocol. Two to three hours after transfection, cells were washed and refed DMEM without serum and treated with 2 nM R1881 for 48 h prior to collecting cell lysates. Corresponding untreated cells were used as negative controls.

Bioluminescence Activity of *Gaussia* Luciferase in Lysates from Hep3B Cells Transfected with Gluc1-AR and JunD-Gluc2:

*Gaussia* luciferase activity was measured in 25 µl of Hep3B cell lysates from R1881-treated or untreated control cells using a *Gaussia* luciferase assay kit from New England Biolabs (Ipswich, Mass.), following the manufacturer-supplied protocol. Bioluminescence activity of the lysate-substrate mixture was read on a single tube Monolight 2010 luminometer (Analytical Luminescence Laboratory, Spaarks, Md.) at 480 nm.

Immunocytochemistry:

LNCap cells were grown in F1C4 medium on coverslips for 2 days followed by 3 days of treatment with 1 nM R1881. Immunofluorescent staining was carried out following a published procedure (31), using primary-secondary antibody pairs JunD-AlexaFlour594 or AR-AlexaFluor488.

Immunoprecipitation:

For whole cell lysates, LNCaP cells were lysed using modified RIPA buffer containing complete protease inhibitors (Roche Applied Sciences, Indianapolis, Ind.). Nuclear and cytoplasmic fractions were prepared and checked for purity using NE-PER Nuclear and Cytoplasmic extraction reagents (Thermo Scientific, Pierce Biotechnology, Rockford, Ill.) following manufacturer-supplied protocols. For immunoprecipitation, lysates were pre-cleared by incubation with 50% Protein A-agarose slurry (Pierce, Rockford, Ill.). Six g of AR antibody and 500 µl pre-cleared lysate (500 µg total protein) were mixed and rocked overnight at 4° C. The immunocomplex was captured with 100 µl of 50% protein A-agarose slurry, then analyzed by western blotting using JunD antibody. The same immunoprecipitation procedure was repeated for capturing the immunocomplex using JunD antibody and western blotting using AR antibody. Proper controls with IgG and protein A-agarose were run in parallel.

Transcriptional Activity of Full Length SSAT-Promoter in siJunD and Vector Control Cell Lines:

The full length (FL) SSAT promoter sequence, kindly provided by Dr. Robert Casero (Johns Hopkins University, Baltimore, Md.), was amplified and cloned into pGL4-basic vector (Promega) with a firefly luciferase reporter gene. This vector, pGL4-SSAT-luc, was transiently transfected into our published (20) JunD-silenced (siJunD) and vector control LNCaP cell lines. Briefly, $5 \times 10^5$ siJunD or vector control LNCaP cells were seeded, then transfected one day later with 1. g pGL4-SSAT-luc DNA construct using Lipofectamine2000 (Invitrogen). After transfection, cells were treated with 1 nM R1881 or left untreated for 72 h, then lysed. Luciferase activity was measured in cell lysates by a luciferase assay system kit (Promega) following the manufacturer-supplied protocol.

Chromatin ImmunoPrecipitation (ChIP) Assay:

ChIP assay was performed using a commercially available ChIP assay kit (Millipore, Billerica, Mass.), essentially following the manufacturer supplied protocol. Briefly, $2 \times 10^6$ LNCaP cells were treated with 1 nM R1881 for 24 h, protein-DNA were cross-linked by addition of formaldehyde (1% final concentration), cells were lysed, and lysates were sonicated for twenty 10 sec pulses with 30 sec intervals to shear the chromatin into approximately 500 bp fragments.

Cross-linked protein-DNA were separated into four parts and immunoprecipitated with either 6 g JunD antibody, 6 g AR antibody, non-specific rabbit IgG or no antibody. Chromatin-antibody complexes were isolated by incubation with 50% salmon sperm DNA/protein-agarose slurry.

Pelleted agarose was eluted and DNA was recovered by phenol/chloroform extraction followed by ethanol precipitation. Two microliters of this DNA was used for each PCR reaction to determine the presence of SSAT promoter fragment bound to either JunD or AR in the immunoprecipitates. DNA primers were designed based on the SSAT gene promoter sequence to cover the complete SSAT promoter sequence (GenBank accession#1103903), as follows:

```
F1: 5'ggaggctgaagcaggagaatc;

R1: 5'ctcactctattgcccaggctggag

F2: 5'cagcctgggcaatagagtgag;

R2: 5'gagatggcgccattgcactcc

F3: 5'gagtgcaatggcgccatctcg;

R3: 5'ctcaccatcttgcccaggctg

F4: 5'cagcctgggcaagatggtgaggcc;

R4: 5'ggagaccctgcagatcccaag

F5: 5'tctgagggtctcccggatcacac;

R5: 5'acctcggcgagtgacggatagg
```

PCR products were run on a 1% agarose gel, purified, cloned into pCR2.1 TOPO vector (Invitrogen) and transformed into TOP100F' competent cells (Invitrogen). At least ten colonies were selected and their plasmids were extracted and sequenced using M13 primer (5' caggaaacagctatgac).

qRT-PCR:

Quantitative RT-PCR analysis of SSAT mRNA levels are performed.

AR and JunD Co-Immunoprecipitate from LNCaP Cell Lysates:

The co-immunoprecipitation of AR and JunD was first shown in whole cell lysates from LNCaP cells grown under normal F10 medium conditions (FIGS. 1A,B).

The immunoprecipitation of AR by rabbit polyclonal antibody against JunD (IP:JunD) was visualized by Western blot analysis using monoclonal antibody against human androgen receptor (WB:AR) as shown in FIG. 1A. The immunoprecipitation of JunD by monoclonal antibody against AR (IP:AR) was visualized by western blotting using antibody against JunD (WB:JunD) as shown in FIG. 1B.

To specifically investigate the effect of androgen, LNCaP cell lysates were prepared after incubation with 1 nM R1881 for 72 h and analyzed for co-immunoprecipitation of AR and JunD. Our published time kinetic studies established that SSAT enzyme activity and cellular ROS production maximizes under these treatment conditions. The corresponding results for co-IP of AR and JunD in nuclear and cytoplasmic fractions of untreated versus androgen-treated LNCaP cells are shown in FIGS. 1C,D. Immunopreciptate using JunD antibody that was probed in a Western blot using AR antibody (FIG. 1C) showed AR-JunD immunocomplex in the nuclear fraction was increased by approximately 3-fold (normalized to β-actin) in 1 nM R1881-treated cells compared to low androgen untreated cells growing in F1C4. Only a small increase was observed in nuclear fractions by IP:AR,WB:JunD (FIG. 1D). This may be due to a difference between the nature of interaction between JunD with its antibody as compared to that between AR and its antibody. No difference in AR-JunD immunocomplex was observed in cytoplasmic fractions of R1881-treated versus untreated cells.

Androgen Induces Nuclear Translocation of JunD in LNCaP Cells:

To further investigate the effect of androgen treatment on JunD activity in LNCaP cells, immunofluorescence staining was performed to determine JunD localization in untreated versus androgen (1 nM R1881) treated LNCaP cells. Representative pictures for each condition are shown in FIG. 2. In untreated LNCaP cells, JunD is mostly dispersed in the cytoplasm with negative staining for the nuclei (FIG. 2A). After R1881 treatment, a substantial amount of JunD translocates into the nucleus as shown in FIG. 2B. Using AR antibody and its related fluorescence-tagged secondary antibody, the translocation of AR into the nucleus in R1881-treated LNCaP cells also was observed under the same condition, which is consistent with observation reported elsewhere. These data indicate tha androgen induces simultaneous translocation of JunD and AR into cell nuclei.

Expression of Gluc1-AR and JunD-Gluc2 in Hep3B Cells:

Because Hep3B cells do not have endogenous AR, this cell line was chosen as a model for AR and JunD interaction studies using a Protein Complementation Assay (PCA) developed by Remy and Michnick (30). This technique is based on reconstitution of the reporter enzyme *Gaussia* luciferase in live cells. The gene coding for the enzyme was split into two sections: N-terminal section (Gluc1) and C-terminal section (Gluc2). Gluc1 and Gluc2 sequences were separately fused to the N-terminus of AR (Gluc1-AR) and the C-terminus of JunD (JunD-Gluc2), respectively, as shown schematically in FIG. 3A.

To verify in-frame fusion of Gluc1-AR and JunD-Gluc2, cell lysates from Hep3B cells transfected with Gluc1-AR or JunD-Gluc2 were analyzed by western blotting. FIG. 3B shows Western blot analysis using monoclonal antibody against AR. Hep3B cells alone (FIG. 3B, lane 1) or Hep3B cells transfected with control vector pcDNA3.1 (FIG. 3B, lane 2) do not show any protein band related to AR. However, expression of the fusion protein (Gluc1-AR) is observed in cells transfected with Gluc1-AR (FIG. 3B, lane 3). As AR is fused at the C-terminal end of Gluc1, presence of the AR band in the western blot confirms the in-frame fusion of AR with Gluc1. Similarly, presence of the C-terminal portion of *Gaussia* luciferase in the western blot of lysate from Hep3B cells transfected with JunD-Gluc2 using polyclonal antibody against *Gaussia* luciferase confirms the in-frame fusion of JunD with Gluc2 (FIG. 3C, lane 3). Hep3B cells alone or Hep3B cells transfected with control vector pCI (FIG. 3C, lanes 1 and 2 respectively) neither expected nor showed any band related to the *Gaussia* luciferase. β-actin was used for protein loading control (FIGS. 3B, C). In-frame gene fusions (Gluc1-AR and JunD-Gluc2) were also confirmed by sequencing using specific primers across the fusion junctions in both vectors.

Bioluminescence Activity of Reconstituted *Gaussia* Luciferase in Hep3B Cells Co-Transfected with Gluc1-AR and JunD-Gluc2 is Markedly Enhanced by Androgen Treatment:

Cell lysates from Hep3B cells that were co-transfected with both Gluc1-AR and JunD-Gluc2 with or without treatment with androgen (R1881) were collected 48 h after transfection and analyzed for *Gaussia* luciferase bioluminescence activity. Results are shown in FIG. 3D. Lysates from co-transfected cells that were not treated with androgen (−R1881=minus R1881) showed very low *Gaussia* luciferase activity. Lysates from co-transfected cells that were treated with 2 nM R1881 (+R1881=plus R1881) showed significantly higher *Gaussia* luciferase activity (>5 fold, $P<10^8$) than the untreated co-transfected cells. Cells transfected with either of the fusion constructs Gluc1-AR and JunD-Gluc2 individually did not show any measurable *Gaussia* luciferase activity (data not shown) confirming that the enzyme activity is only observed after both fragments Gluc1 and Gluc2 associate with each other (30). Minor baseline reporter enzyme activity in cell lysates from androgen-untreated co-transfected cells (−R1881) might be due to interaction of residual activated-AR remaining after the transfection process, which was performed in medium containing serum that was not stripped of androgen. These data clearly establish an interaction of JunD and androgen-activated AR in situ that brings their corresponding fusion proteins Gluc1 and Gluc2 together to reconstitute *Gaussia* luciferase activity.

Activated Androgen Receptor Requires JunD to Induce Transcriptional Activity of the SSAT Promoter:

The effect of AR activation by androgen on transcriptional activity of full length SSAT promoter and the necessity of JunD for such effect was studied in LNCaP cells stably transfected with either junD silenced (siJunD) or control vector that were then transiently transfected with a full length SSAT promoter-firefly luciferase reporter vector (FLSSAT-luc) followed by androgen treatment (FIGS. 4A,B). Androgen treatment (1 nM R1881) caused a significant>16-fold increase in SSAT promoter activity in vector control LNCaP cells (Control) compared to corresponding untreated cells (FIG. 4A, P=0.03). Although androgen also caused a small increase in SSAT promoter activity in siJunD cells, where JunD expression is 70% suppressed, the extent of induction was not statistically significant (FIG. 4A, P=0.16). SSAT mRNA levels in LNCaP cells determined by qRT-PCR assay are shown in FIG. 4B. There is an androgen-induced increase in SSAT mRNA (~10-fold) in siJunD cells, but this increase is much less than that observed in vector control cells (~25-fold). Thus, even though some increase in SSAT mRNA expression in siJunD cells was observed, the increase is not enough to significantly enhance cellular SSAT protein expression as evident from the insignificant increase in luciferase reporter expression.

JunD Binds to the SSAT Promoter in situ by Chromatin ImmunoPrecipitation (ChIP) Assay:

ChIP assay was performed in LNCaP cells with R1881 treatment to ascertain if activated AR and/or JunD bind to the SSAT promoter site using primer sets targeted to identify the SSAT promoter sequence in the immunoprecipitates (see Materials and Methods). ChIP assay was performed under conditions where only protein-DNA and not protein-protein interactions can be detected (reviewed in 32). Under these conditions, the only PCR product obtained using those primers was from chromatin fragment(s) immunoprecipitated by rabbit polyclonal antibody against JunD using the F1R1 primer pair as shown in FIG. 5A. Using the same F1R1 primer pair, no PCR product was obtained from immunoprecipitates obtained by monoclonal antibody against AR, nor from the non-specific IgG and no antibody controls. None of the other primer pairs yielded any PCR product from either JunD-, AR- or IgG-immunoprecipitated chromatin fragments.

The sequence data obtained from the PCR product that was cloned in pCR2.1TOPO indicates the existence of JunD binding sites at −574 to −651 bp upstream in the SSAT promoter sequence that contains multiple half sites (TGA) of the AP1 consensus sequence (TGA$^{G/C}$TCA) (FIG. 5B).

Example 3

Validation of Compounds that are Active in Reducing ROS and Inhibiting Growth of CaP Cells in Culture Graded concentrations of each of the 8-10 designed peptides identified herein are further tested for their ability to inhibit growth of androgen-dependent LNCaP and LAPC-4 cells using a DNA fluorescence assay and androgen-induced ROS using DCFH dye oxidation assay.

Since inhibiting AR-activation by androgen binding, in some embodiments, also blocks JunD-AR complex formation and SSAT activation, the compounds are tested for their effects on androgen binding to the AR ligand binding domain (AR-LBD) using a published fluorescence polarization assay performed routinely in the laboratory using the Polar-Screen™ Androgen Receptor Competitor Assays kit (Catalog #P3018) from Invitrogen (Carlsbad, Calif.) following manufacturer supplied protocol. Bicalutamide is used as a positive control. This assay has been well-standardized in the laboratory and has been extensively used for studies of AR-binding studies of an anti-androgen previously developed in the laboratory.

Identification of Compounds Including but not Limited to Those Described Herein from Efficacy Studies In Vivo in Human CaP Xenografts and Transgenic Animal Models Developing Spontaneous CaP:

Pharmacokinetics and Determination of Oral Bioavailability:

A LC-MS protocol for at least 3-4 of the compounds described herein are standardized using the 3P Laboratory facility in UWCCC and used to determine pharmacokinetics of oral versus intravenous (iv) administration to confirm that the compounds are not fast-metabolized and compare oral bioavailability of the compounds. For each compound, a single dose of 1 mg/kg is administered either orally or iv. Blood and tissues are collected at 7 time points from 15 minutes to 24 hours (n=3 mice per time-point per route of administration) and assayed by the LC-MS method.

Determination of Maximum Tolerated Dose (MTD):

Studies are performed for a daily oral regimen of the compound that shows the best oral bioavailability, based on the results collected, to determine target dose $LD_{10}$, which will be the MTD. Multiple doses of the agent will be tested to identify $LD_{10}$ in ICR white mice, using an estimated 30 mice. Confirming MTD studies are performed in the nude mice and TRAMPxFVB mice strains used in efficacy studies: A group of mice are treated at the determined MTD. If 15% or less of the drug-treated mice (i.e., #3/20 mice) expire in 4 weeks, the dose is declared tolerable. If greater than 15% mice expire, we declare the initial dose to be greater than the MTD and we accrue another 20 mice to be administered a lower dose.

Examination of Anti-Cancer Activity in Human CaP Xenografts:

Efficacy of the test agent is determined against a CaP cell xenograft(s). The cell line for xenograft is chosen from the results of earlier performed studies. The cells are subcutaneously implanted in nude mice and drug efficacy is determined by routinely measuring tumor volumes following an established protocol.

Assessment of Anti-Tumor Activity in the TRAMP Model:

The compounds described herein are tested for their chemopreventive effect in the TRAMP animal model. Efficacy is determined by ability to delay tumor progression and increase survival time of the TRAMP animals. Briefly, TRAMPxFVB mice are randomized at 8 weeks of age to vehicle control (n=20) versus agent at MTD (n=20). During treatment, the mice are palpated for a gross measure of masses in the lower abdominal region that is recorded once weekly. Twenty-four weeks after the initiation of treatment, when the majority of control mice have demonstrable prostate tumors, mice are sacrificed and the prostate lobes are removed and fixed in 10% formalin and prepared for histological analysis. A subset of 10 mice per group are also followed by imaging performed routinely using a Varian (Walnut Creek, Calif.), Magnex Scientific Product, 4.7-Telsa self-shielded gradient system type model SGRAD 205/120/HD/S 3D micro-MRI scanner. The imaging is performed at the start of treatment, again at 12 weeks of age, then every 1 to 2 weeks thereafter for a longitudinal analysis of prostate tumor growth. The palpation and imaging data is used to determine time to first tumor and survival of these animals are followed for determination of drug efficacy.

Clinical Trial of a Compound Described Herein for the Treatment of Prostate Cancer Purpose: This is a clinical trial of an orally administered drug described herein in patients whose disease has progressed following 1 prior chemotherapy regimen for metastatic prostate cancer.

Primary Outcome Measures:

PSA50 response rate of oral test compound as monotherapy in the treatment of metastatic prostate cancer and safety and tolerability of oral test compound in patients with metastatic prostate cancer.

Secondary Outcome Measures:

Median time to progression in patients with metastatic prostate cancer and response rate according to RECIST criteria in patients with measurable metastatic prostate cancer who are treated with test compound.

Eligibility

Ages Eligible for Study: 18 years and older

Genders Eligible for Study: Male

Criteria

Inclusion Criteria:

Diagnosed with radiographically-documented metastatic prostate cancer that has progressed.

Patients must demonstrate evidence of progressive disease based on 1 of the following criteria: 1) Progressive measurable disease, or 2) Progressive rise in PSA level (2 consecutive rises from a prior reference level), or 3) Development of new lesions on bone scan.

Must have received and progressed during or following 1 prior chemotherapy regimen for metastatic disease; or, must have discontinued prior systemic therapy because of poor tolerance or other adverse effects; or, must have refused chemotherapy treatment. Patients having undergone more than 1 prior chemotherapy regimen may be admitted at the discretion of the sponsor.

Eastern Cooperative Oncology Group (ECOG) performance status of 0 to 2.

Baseline serum PSA level of ≥10 ng/mL

Exclusion Criteria:

Received any anti-cancer medications in the 30 days before receiving their first dose of study medication except for GnRH agonists and bisphosphonates.

Any unresolved toxicity greater than or equal to Grade 2 from previous anti-cancer therapy, except for stable chronic toxicities not expected to resolve, such as peripheral neurotoxicity.

Other embodiments of the present disclosure will be apparent to those skilled in the art from consideration of the specification and practice of the embodiments disclosed herein. It is intended that the specification and examples be considered as exemplary only, being indicated by the following claims.

What is claimed is:

1. A compound having the structure of Formula (I):

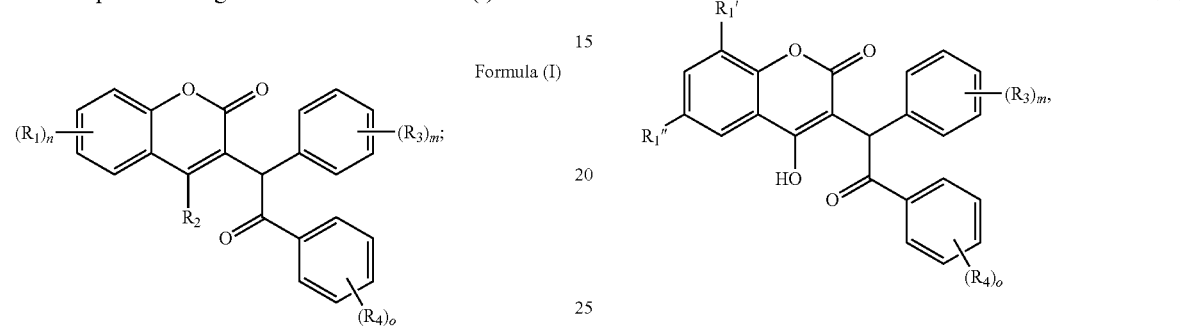

wherein:

each $R_1$, $R_3$ and $R_4$ are each independently selected from H, —CN, —NO$_2$, —OH, —CF$_3$, —OCF$_3$, —NR$_6$R$_6$, C$_3$-C$_8$cycloalkyl, C$_1$-C$_6$heteroalkyl, C$_1$-C$_6$haloalkyl, C$_2$-C$_8$heterocycloalkyl, optionally substituted aryl, optionally substituted O-aryl, optionally substituted heteroaryl, —N=N-aryl, —NHS(=O)$_2$R$_5$, —S(=O)$_2$N(R$_6$)$_2$, —N(R$_6$)S(=O)$_2$N(R$_6$)$_2$, —C(=O)CF$_3$, —C(=O)NHS(=O)$_2$R$_5$, —S(=O)$_2$NHC(=O)R$_5$, —N(R$_6$)$_2$, —N(R$_6$)C(=O)R$_6$, —N(R$_6$)C(=O)N(R$_6$)$_2$, —N(R$_6$)C(=O)OR$_5$, —CO$_2$R$_6$, —C(=O)R$_6$, —OC(=O)R$_5$, —OC(=O)N(R$_6$)$_2$, —CON(R$_6$)$_2$, —SR$_6$, S(=O)$_2$OH—S(=O)R$_5$, and —S(=O)$_2$R$_5$; wherein at least one $R_1$ is not H;

each $R_5$ is independently selected from C$_1$-C$_6$alkyl, C$_1$-C$_6$haloalkyl, C$_3$-C$_8$cycloalkyl, aryl, and benzyl;

each $R_6$ is independently selected from H, C$_1$-C$_6$alkyl, C$_1$-C$_6$haloalkyl, C$_3$-C$_8$cycloalkyl, aryl, and benzyl;

$R_2$ is selected from H, OH, OC(=O)C$_1$-C$_6$alkyl, or OC(=O)H;

n is an integer selected from 1-4; and m and o are each independently an integer selected from 0-5; or a pharmaceutically acceptable salt, solvate, or prodrug thereof.

2. The compound of claim 1 wherein $R_2$ is OH.

3. The compound of claim 1 wherein $R_1$ is S(=O)$_2$OH.

4. The compound of claim 1 wherein $R_1$ is —N=N-aryl.

5. The compound of claim 4 wherein aryl is naphthyl.

6. The compound of claim 1 wherein $R_1$ is OH.

7. The compound of claim 1 wherein n is 1.

8. The compound of claim 1 wherein $R_3$ is S(=O)$_2$OH.

9. The compound of claim 1 wherein $R_4$ is —N=N-aryl.

10. The compound of claim 9 wherein aryl is naphthyl.

11. The compound of claim 1 selected from the group consisting of:

-continued

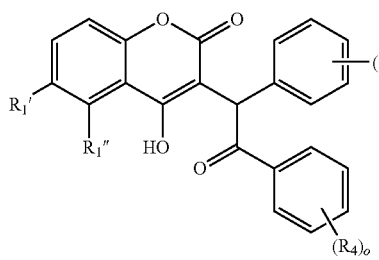

Formula (IE)

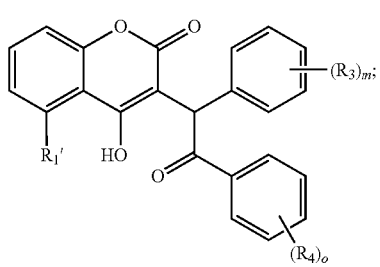

Formula (ID)

wherein $R_1'$ and $R_1''$ are each independently selected from —CN, —NO$_2$, —OH, —CF$_3$, —OCF$_3$, NR$_6$R$_6$, C$_3$-C$_8$cycloalkyl, C$_1$-C$_6$heteroalkyl, C$_1$-C$_6$haloalkyl, C$_2$-C$_8$heterocycloalkyl, optionally substituted aryl, optionally substituted O-aryl, optionally substituted heteroaryl, —N=N-aryl, —NHS(=O)$_2$R$_5$, —S(=O)$_2$N(R$_6$)$_2$, —N(R$_6$)S(=O)$_2$N(R$_6$)$_2$, —C(=O)CF$_3$, —C(=O)NHS(=O)$_2$R$_5$, —S(=O)$_2$NHC(=O)R$_5$, —N(R$_6$)$_2$, —N(R$_6$)C(=O)R$_6$, —N(R$_6$)C(=O)N(R$_6$)$_2$, —N(R$_6$)C(=O)OR$_5$, —CO$_2$R$_6$, —C(=O)R$_6$, —OC(=O)R$_5$, —OC(=O)N(R$_6$)$_2$, —CON(R$_6$)$_2$, —SR$_6$, —S(=O)R$_5$, or —S(=O)$_2$R$_5$; and each R$_5$ is independently selected from C$_1$-C$_6$alkyl, C$_1$-C$_6$haloalkyl, C$_3$-C$_8$cycloalkyl, aryl, and benzyl; and each R$_6$ is independently selected from H, C$_1$-C$_6$alkyl, C$_1$-C$_6$haloalkyl, C$_3$-C$_8$cycloalkyl, aryl, and benzyl.

12. A compound selected from the group consisting of:

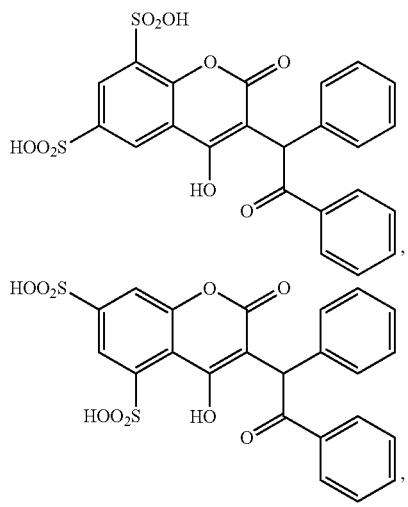

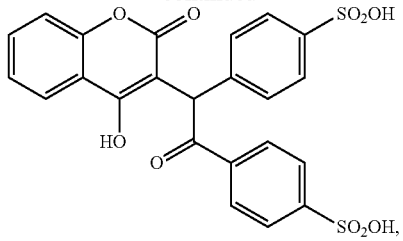

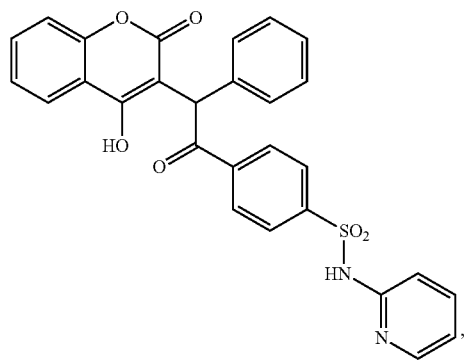

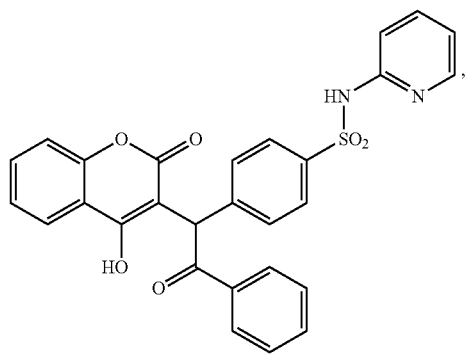

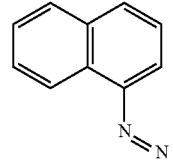

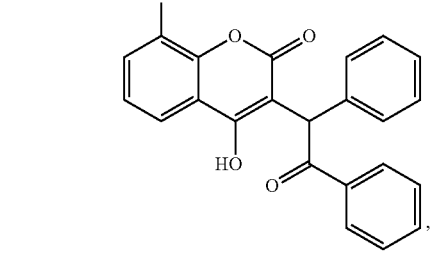

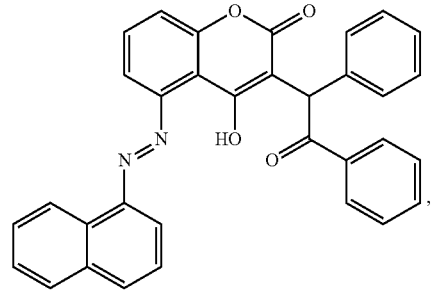

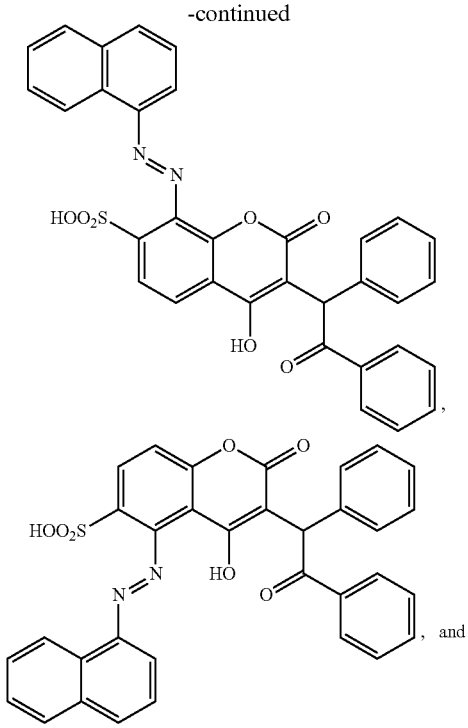
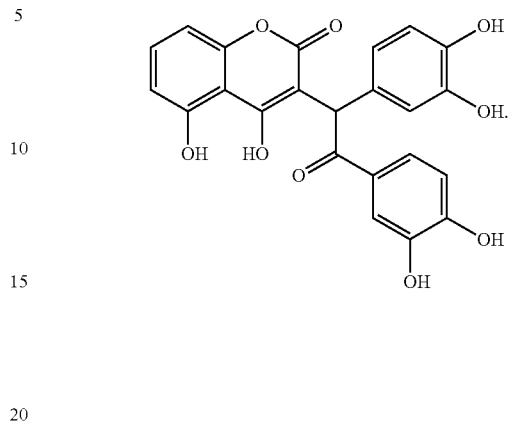
13. A pharmaceutical composition comprising a compound of claim 1 or a pharmaceutically acceptable salt, solvate, or prodrug thereof and a pharmaceutically acceptable binder, excipient, or diluent thereof.
* * * * *

SEQUENCE LISTING

```
<160> NUMBER OF SEQ ID NOS: 1

<210> SEQ ID NO 1
<211> LENGTH: 300
<212> TYPE: DNA
<213> ORGANISM: Homo sapiens
<220> FEATURE:
<221> NAME/KEY: misc_feature
<222> LOCATION: (1)..(300)
<223> OTHER INFORMATION: SSAT
<300> PUBLICATION INFORMATION:
<308> DATABASE ACCESSION NUMBER: NCBI / 1103903
<309> DATABASE ENTRY DATE: 1996-05-04
<313> RELEVANT RESIDUES IN SEQ ID NO: (541)..(840)

<400> SEQUENCE: 1
ggtggcaggt gggaggctga agcaggagaa tcacttgaac ccaggaggag gcggaggttg      60
```

```
cagtgagccg agattgtgcc attgcactcc agcctgggca atagagtgag actctgttta    120
aaaaaaaaat atatatatat atatatataa tatatatata ttatatatat atatataata    180
tatatatata ttatatatat atatgtaatg ttggttgcat ctatccattc atgacaatgg    240
aaaagcataa tgtgattcac tgccatgaaa aacattcaaa cttcttaggg ttctaggctt    300
```